(12) United States Patent
Capes

(10) Patent No.: US 6,217,550 B1
(45) Date of Patent: Apr. 17, 2001

(54) SINGLE-USE SYRINGE

(75) Inventor: David Francis Capes, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/338,235

(22) Filed: Jun. 22, 1999

Related U.S. Application Data

(63) Continuation-in-part of application No. 09/274,117, filed on Mar. 23, 1999, which is a continuation-in-part of application No. 09/249,431, filed on Feb. 12, 1999, which is a continuation-in-part of application No. 09/124,447, filed on Jul. 29, 1998.

(51) Int. Cl.$^7$ .................................................. A61M 5/00
(52) U.S. Cl. ........................ 604/110; 604/181; 604/228; 604/218
(58) Field of Search .................................. 604/240, 181, 604/187, 218, 110, 263, 228

(56) References Cited

U.S. PATENT DOCUMENTS

| | | | |
|---|---|---|---|
| 2,158,593 | 5/1939 | Scrimgeour | 128/221 |
| 3,179,107 | 4/1965 | Clark | 128/221 |
| 4,676,530 | 6/1987 | Nordgren et al. | 285/93 |
| 5,004,460 * | 4/1991 | Gimeno | 604/228 |
| 5,149,323 * | 9/1992 | Colonna | 604/110 |
| 5,181,912 * | 1/1993 | Hammett | 604/110 |
| 5,205,833 | 4/1993 | Harsh et al. | 604/240 |
| 5,215,524 * | 6/1993 | Vallelunga et al. | 604/110 |
| 5,226,882 * | 7/1993 | Bates | 604/110 |
| 5,336,200 * | 8/1994 | Streck et al. | 604/198 |
| 5,383,857 | 1/1995 | Levitov | 604/110 |
| 5,489,272 * | 2/1996 | Wirtz | 604/110 |
| 5,605,544 | 2/1997 | Tsao | 604/110 |
| 5,738,655 * | 4/1998 | Vallelunga et al. | 604/110 |
| 5,833,660 * | 11/1998 | Nathan et al. | 604/110 |
| 6,013,056 * | 1/2000 | Pettersen | 604/110 |

FOREIGN PATENT DOCUMENTS

| | | |
|---|---|---|
| 0 364 777 | 4/1990 | (EP) . |
| 1 286 690 | 8/1972 | (GB) . |
| 2 256 146 | 4/1998 | (GB) . |
| 2 318 060 | 4/1998 | (GB) . |
| WO 96/30076 | 10/1996 | (WO) . |
| WO 97/31665 | 9/1997 | (WO) . |

\* cited by examiner

Primary Examiner—Richard K. Seidel
Assistant Examiner—Cris Rodriguez
(74) Attorney, Agent, or Firm—John L. Voellmicke

(57) ABSTRACT

A syringe includes a barrel having a fluid chamber, a proximal end, a distal end and an elongated tip extending from the distal end and having a passageway therethrough in fluid communication with the chamber. A plunger is provided for drawing fluid into and out of the barrel. The plunger includes an elongated plunger rod having a proximal portion and a distal portion connected by a breakable connection. The breakable connection is strong enough to hold the proximal portion and distal portion together during normal use of the syringe and breakable upon application of additional force to the proximal portion.

23 Claims, 26 Drawing Sheets

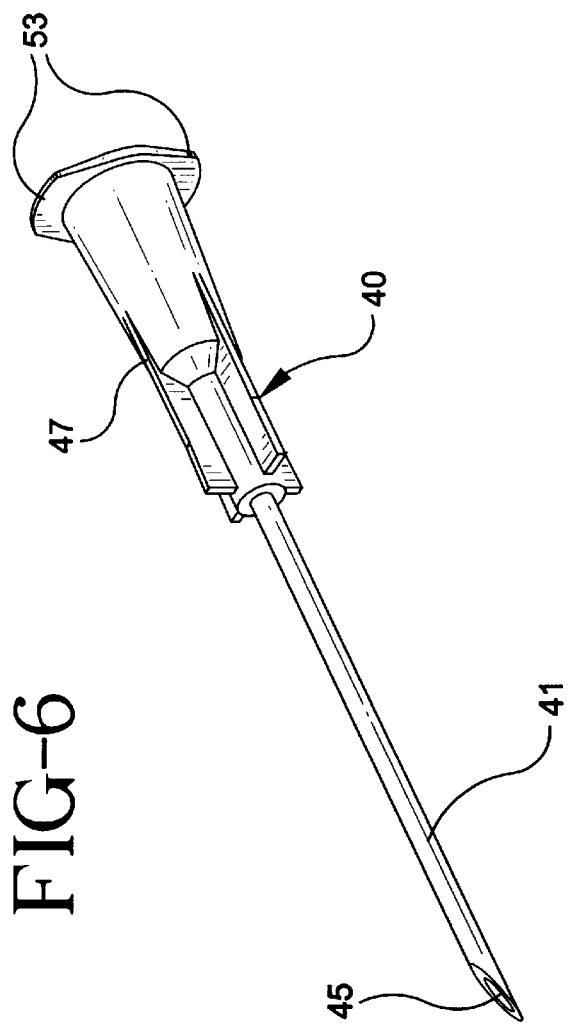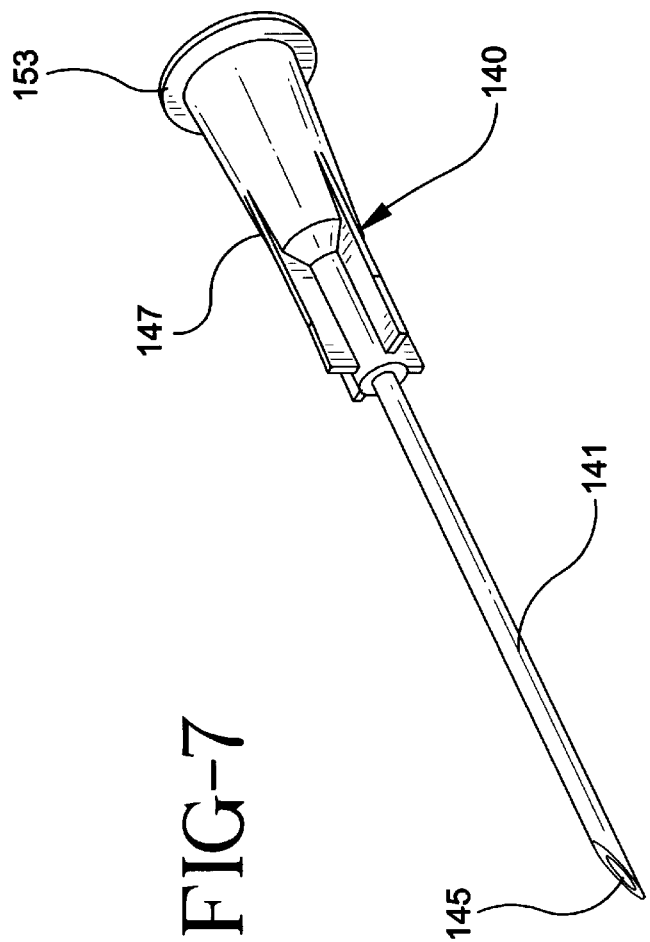

SINGLE-USE SYRINGE

CROSS-REFERENCE TO RELATED APPLICATIONS

This patent application is a continuation-in-part of U.S. patent application Ser. No. 09/274,117 filed on Mar. 23, 1999 which is a continuation-in-part of U.S. patent application Ser. No. 09/249,431 filed on Feb. 12, 1999 which is a continuation-in-part of U.S. patent application Ser. No. 09/124,447 filed on Jul. 29, 1998.

FIELD OF THE INVENTION

The present invention relates to a syringe having a breakable plunger rod to prevent further use of the syringe after fluid delivery or injection. The present invention also relates to fluid transfer devices having improved needle attaching features and in particular, structure to help prevent the removal of a hypodermic needle assembly from a fluid transfer device such as a hypodermic syringe.

BACKGROUND

Throughout the world the re-use of hypodermic syringe products which are intended for single-use only is instrumental in drug abuse and in the transfer of contagious diseases. Intravenous drug users who routinely share and re-use syringes are a high-risk group with respect to the AIDS virus. Also, the effects of multiple use are a major concern in some countries where the repeated use of syringe products during mass inoculation programs may be responsible for the spread of many diseases. Syringes are often recycled in developing countries without proper sterilization.

Many attempts have been made to remedy this problem. Some designs involve the inclusion of structure which will allow the destruction or defeating of the syringe function through a conscious act by the user, such as breaking a syringe or one of its components. In addition, there are single-use hypodermic syringes which become incapable of further use automatically upon delivery of the medication without any additional act on the part of the user. Such syringes are taught in U.S. Pat. No. 4,961,728.

With single-use syringes using needle assemblies having a hub attached to a needle cannula there is a need to prevent the removal of the needle assembly after the use of the single-use syringe so that the needle assembly cannot be used again with other syringes. In addition to preventing the removal of the needle assembly, there is also a need for structure which will allow the easy attachment of the needle assembly to the syringe so that the needle assembly may be attached at the time of use and an appropriately sized needle may be used.

SUMMARY OF THE INVENTION

A fluid transfer device comprises a barrel having a fluid chamber, a proximal end, a distal end and an elongated tip extending from the distal end having a passageway therethrough in fluid communication with the chamber. A collar surrounds the tip. For the purposes of the present invention collar is intended to include not only continuous structures but also discontinuous structures such as a wall with gaps in its structure. At least one deflectable locking tab projects radially inwardly from the collar and is adapted to engage the hub of a needle assembly to prevent the removal of the needle assembly away from the tip. The locking tab is configured to allow assembly of the needle assembly to the barrel through axial motion of the hub toward the barrel.

Another embodiment of the present fluid transfer device includes a needle assembly having a cannula with a proximal end, a distal end, and a lumen therethrough. A hub includes an open proximal end with a cavity therein and a distal end is joined to the proximal end of the cannula so that the lumen is in fluid communication with the cavity. The hub includes an outside surface. A barrel having a fluid chamber includes an open proximal end, a distal end and an elongated frusto-conically shaped tip extending from the distal end having a passageway therethrough in fluid communication with the chamber. A collar surrounding the tip includes a plurality of deflectable locking tabs projecting radially and proximally inwardly from the collar defining an inner aperture surrounding the tip. The tip extends distally beyond the aperture defined by the locking tabs. The needle assembly is connected to the barrel so that the elongated tip of the barrel is in the cavity of the hub and the outside surface of the hub is adjacent to the inner aperture defined by the locking tabs so that the locking tabs prevent removal of the needle assembly from the barrel through contact between the locking tabs and the outside surface of the hub.

Another embodiment of the present fluid transfer device includes means on the hub between the distal end of the hub and the proximal end of the hub for allowing the hub to break upon application of a bending force to the hub. Such means includes a fracturable section between the proximal end and the distal end of the hub such as an annular discontinuity on the outside surface of the hub or an annular discontinuity in the cavity of the hub. The fracturable section is provided to prevent removal of the needle assembly from the fluid transfer device by allowing the hub to break if an excessive bending force is applied to the hub.

Another embodiment of the present invention includes a plunger having an elongated plunger rod, a proximal portion and a distal portion. The distal portion includes a stopper slidably positioned in fluid-tight engagement with an inside surface of the barrel for drawing fluid into and out of the barrel by movement of the plunger relative to the barrel. The plunger further includes means for allowing the connection between the proximal portion of the plunger rod and the distal portion of the plunger rod to break upon application of additional force to the proximal portion. The means for allowing the connection between the proximal portion of the plunger and the distal portion to break can include an axial projection on one of the proximal portion and the distal portion having at least one transverse protuberance projecting therefrom. The protuberance is connected to the other of the proximal portion and the distal portion and the breakable connection is on the protuberance. Preferably, there are a plurality of protuberances and more preferably, there are four protuberances with two protuberances projecting from one side of the axial projection and two protuberances projecting from another side of the axial projection, preferably in substantially opposite directions.

Another embodiment of the present invention includes a plunger having a distally directed extension on the distal portion of the plunger rod shaped to fit within the passageway of the tip of the syringe barrel when the plunger is positioned distally with respect to the barrel. The purpose of the distally directed extension is to drive as much medication out of the syringe barrel as possible and therefore reduce wasted medication.

BRIEF DESCRIPTION OF THE DRAWINGS

FIG. 6 is a perspective view of the needle assembly of FIG. 2;

FIG. 7 is an alternative needle assembly, similar to the needle assembly of FIG. 6;

DETAILED DESCRIPTION

Figure 1:
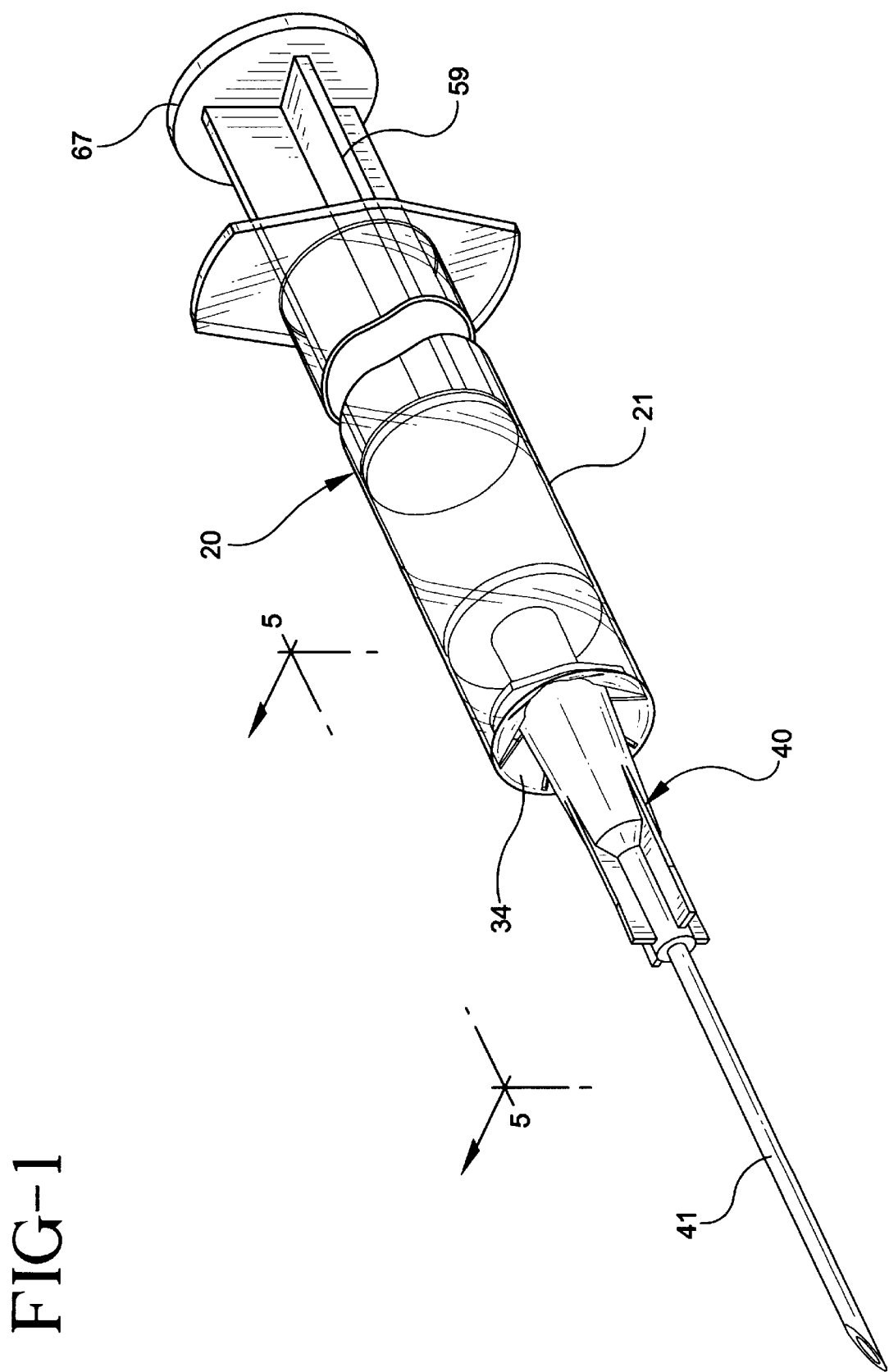
FIG. 1 is a perspective view of a fluid transfer device of the present invention with a needle assembly attached.
Figure 2:
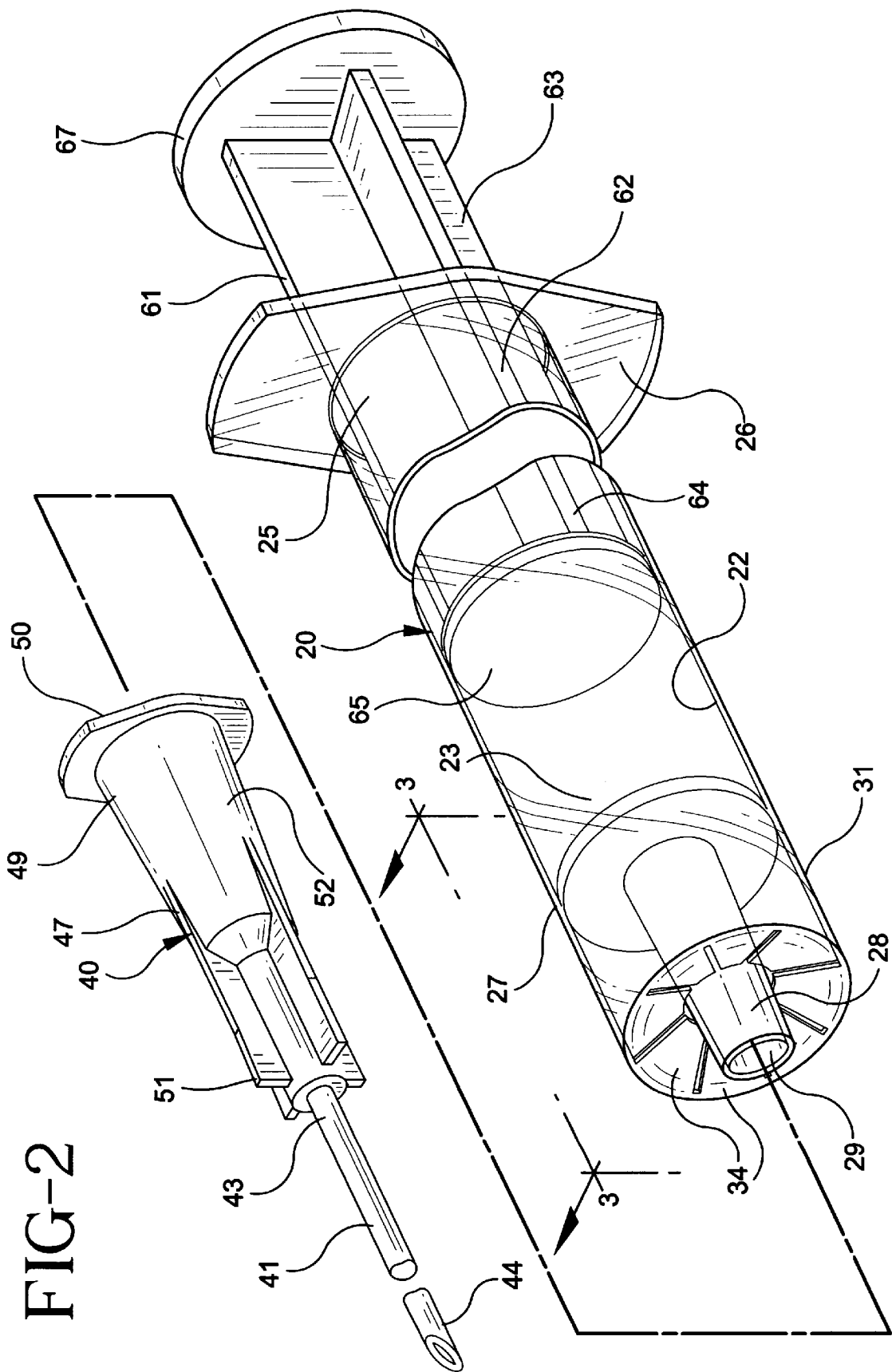
FIG. 2 is an exploded prospective view of the fluid transfer device and needle assembly of FIG. 1.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1–7 a fluid transfer device such as syringe 20 includes a barrel 21 having a barrel inside surface 22, a fluid chamber 23, a proximal end 25, a distal end 27 and an elongated tip 28 extending from the distal end having a passageway 29 therethrough in fluid communication with the chamber. In this embodiment the elongated tip is preferably frusto-conically shaped.

Barrel 21 further includes a collar 31 having an inside surface 32 and at least one deflectable locking tab projecting radially inwardly from the collar. The collar preferably but not necessarily surrounds the tip. In this preferred embodiment, there are a plurality of locking tabs 34 projecting radially and proximally inwardly from the inside surface. In this preferred embodiment a distal end 30 of elongated tip 28 extends distally beyond distal end 33 of the collar. It is preferable that the collar and the locking tabs are integrally formed of a single material preferably a metal such as stainless steel or a plastic material such as polypropylene. Also, the collar can be made of thermoplastic material and the locking tabs of metal, such as stainless steel attached to the collar.

The fluid transfer device of the present invention is intended to be used with a needle assembly 40 including a cannula 41 having a proximal end 43 a distal end 44 and a lumen 45 therethrough. The needle assembly also includes a hub 47 having an open proximal end 49 with a cavity 50 therein, and a distal end 51 joined to proximal end 43 of cannula 41 so that lumen 45 is in fluid communication with cavity 50. Hub 47 also includes outside surface 52. The hub in this embodiment preferably, but not necessarily, includes at least one projection extending radially outwardly from outside surface 52 of the hub. This embodiment includes two projections 53. It is within the purview of the present invention to include needle assemblies having one-piece construction wherein the cannula and the hub are formed of one piece.

Some prior art syringe barrels include a collar around the distal tip having a thread on the inside surface of the collar. This configuration is often referred to as a locking luer collar. A needle assembly having a hub with outwardly extending projections is placed on the distal end of the syringe by aligning the distal tip of the syringe with a cavity in the hub and moving the needle assembly toward the syringe so that the outward projections of the hub engage the thread. The needle assembly is then rotated or screwed into the locking luer collar so that the needle assembly is held tightly on the distal tip of the syringe barrel through interaction of the locking luer collar thread and the projections on the hub. This is an excellent structure for most applications since it allows for applying the appropriate sized needle assembly at the time of use and for changing needle assemblies during a procedure which may require two or more different sizes. However, for many applications it is not desirable to have structure which provides for the easy removal of the needle assembly. For example, in mass inoculation programs using single-use syringes, a needle assembly which is not removable compliments the syringe assembly which is not reusable. Although most healthcare institutions have procedures for disposal of used fluid transfer devices, an unscrupulous healthcare worker can, if the structure allows, remove the relatively small hypodermic needle assembly before disposing of the larger syringe assembly catheter or I.V. set.

The present invention provides structure to prevent removal of the needle assembly during normal use of the fluid transfer device. In particular, the locking tab projecting radially inwardly from the inside surface of the collar is adapted to engage the outside surface of the hub of the needle assembly to prevent removal of the needle assembly away from the tip of the barrel. The locking tab is configured to allow assembly of needle assembly to the syringe barrel through axial motion of the hub toward the barrel. In use, the needle assembly is connected to the barrel by moving the needle assembly toward the barrel so that elongated tip 28 of the barrel is in cavity 50 of the hub and outside surface 52 of the hub is adjacent to locking tabs 34 so that the locking tab prevents removal of the needle assembly from the barrel through contact of the locking tabs with the outside surface of the hub. Accordingly, the force for removal of the needle assembly from the syringe is much higher than the force for installation of the needle assembly to the barrel. This is an important feature of the present invention.

Figure 5:
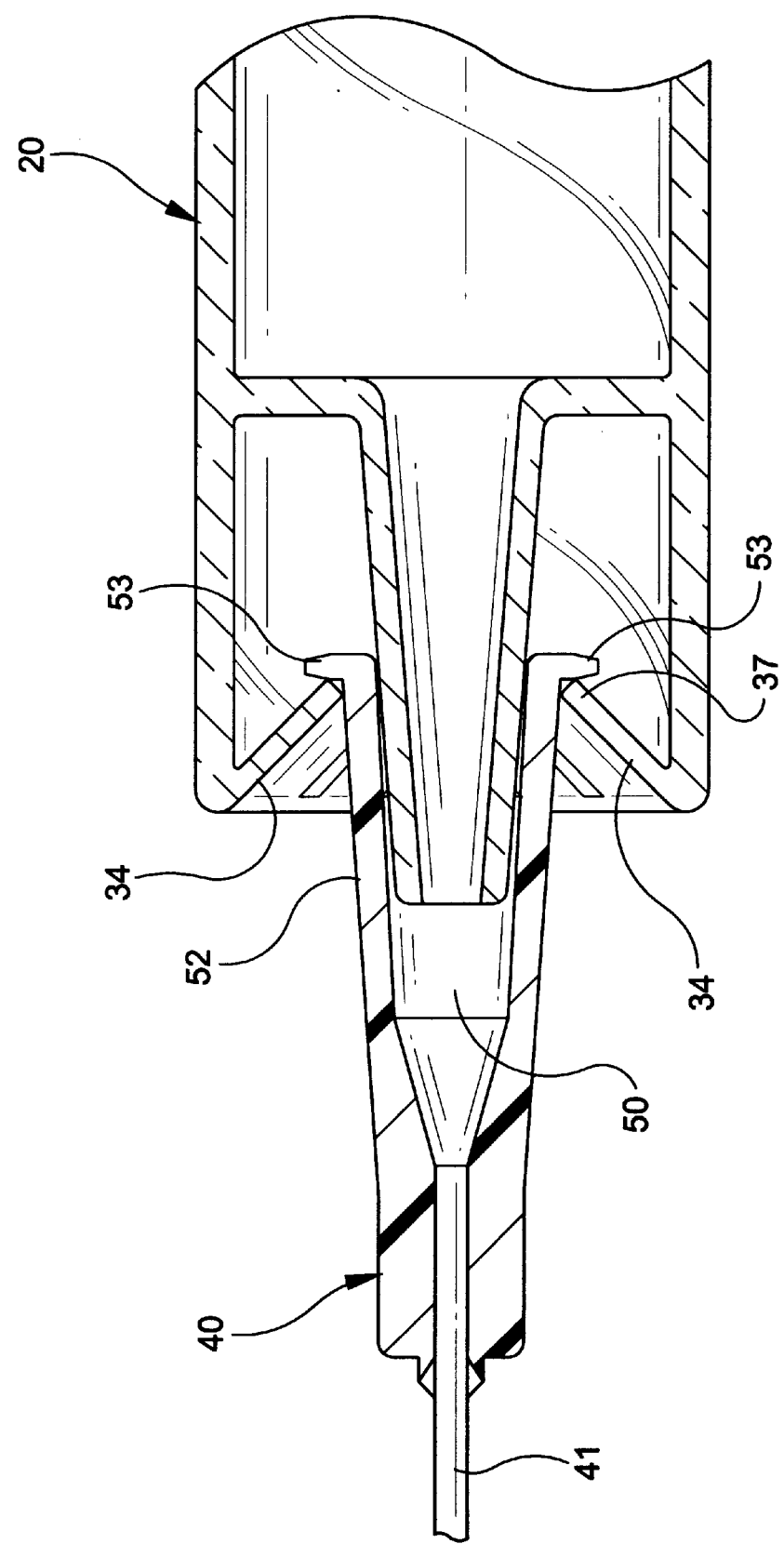
FIG. 5 is an enlarged partial cross-sectional view of the needle assembly and fluid transfer device of FIG. 1 taken along line 5—5.

Although only one locking tab is required for the present invention, the preferred embodiment illustrated herein includes a plurality of locking tabs 34 which are deflected by the proximal end and/or the outside surface of the hub when the needle assembly is installed onto the barrel. Tabs 34 are separated by gaps 35 to allow them to flex more freely and provide for lower forces when attaching the needle assembly to the barrel. The locking tabs include distal ends 37 which in this preferred embodiment describe a opening 39 which is preferably circularly shaped and smaller than the outside surface of the hub and/or the width described by projections 53 so that the locking tabs deflect when the needle assembly is installed onto the barrel. Because the locking tabs are facing radially and proximally inwardly after needle attachment they are very resistant to flexing outwardly to allow the removal of the needle assembly, as best illustrated in FIG. 5. Some portion of the outside surface of the hub preferably describes a dimension which is larger than the opening 39 described by the distal ends 37 of the locking tabs so that an attempt to remove the needle assembly there will not be enough space for the tabs to move towards a position which is perpendicular to the longitudinal axis of the barrel.

In this preferred embodiment, the needle assembly includes projections 53 projecting outwardly from the outside surface of the hub to help prevent removal of the needle assembly from the barrel through contact between the locking tabs and the projections. The present invention can accomplish its purpose without the radial projection or projections on the hub however the projection or projections provide a stronger attachment of the needle assembly to the barrel and allow for more liberal tolerances for the locking tab dimensions.

An alternate needle assembly 140 is illustrated in FIG. 7. This needle assembly is similar to the needle assembly 40 and includes cannula 141 and hub 147. Hub 147 includes one projection 153 extending 360° around the hub. This structure is especially desirable if only one or two locking tabs are used so that it is not necessary to align the projection on the needle hub with the locking tabs since the projection on the hub will always be positioned so that it can contact a locking tab.

The syringe of the present embodiment further comprises a plunger 59 including a plunger rod 61 having an elongated body portion 62 having a proximal end 63, a distal end 64 and a stopper 65 at the distal end. The stopper is slidably positioned in fluid-tight engagement with the barrel inside surface. The plunger rod extends outwardly from proximal end 25 of the barrel. The plunger rod is accessible outside of proximal end 25 of the barrel and is provided to move the stopper along the barrel to force fluid into and out of chamber 23 through passageway 29. Disc-shaped plunger rod flange 67 is provided as a convenient structure for applying forces to move the plunger rod with respect to barrel 21. A flange 26 is also provided at the proximal end of the barrel to facilitate handling and for maintaining the relative position of the barrel with respect to the plunger rod during fluid transfer using known procedures.

It is within the purview of the present invention to include plunger rods and stoppers which are separately formed or integrally formed of the same material or different materials such as in two-color molding, or separately formed of the same or different materials and joined together by mechanical means, adhesives, ultrasonic welding, heat sealing or other suitable means. It is understood that the plunger of the present embodiment merely illustrates these many possibilities.

Figure 8:
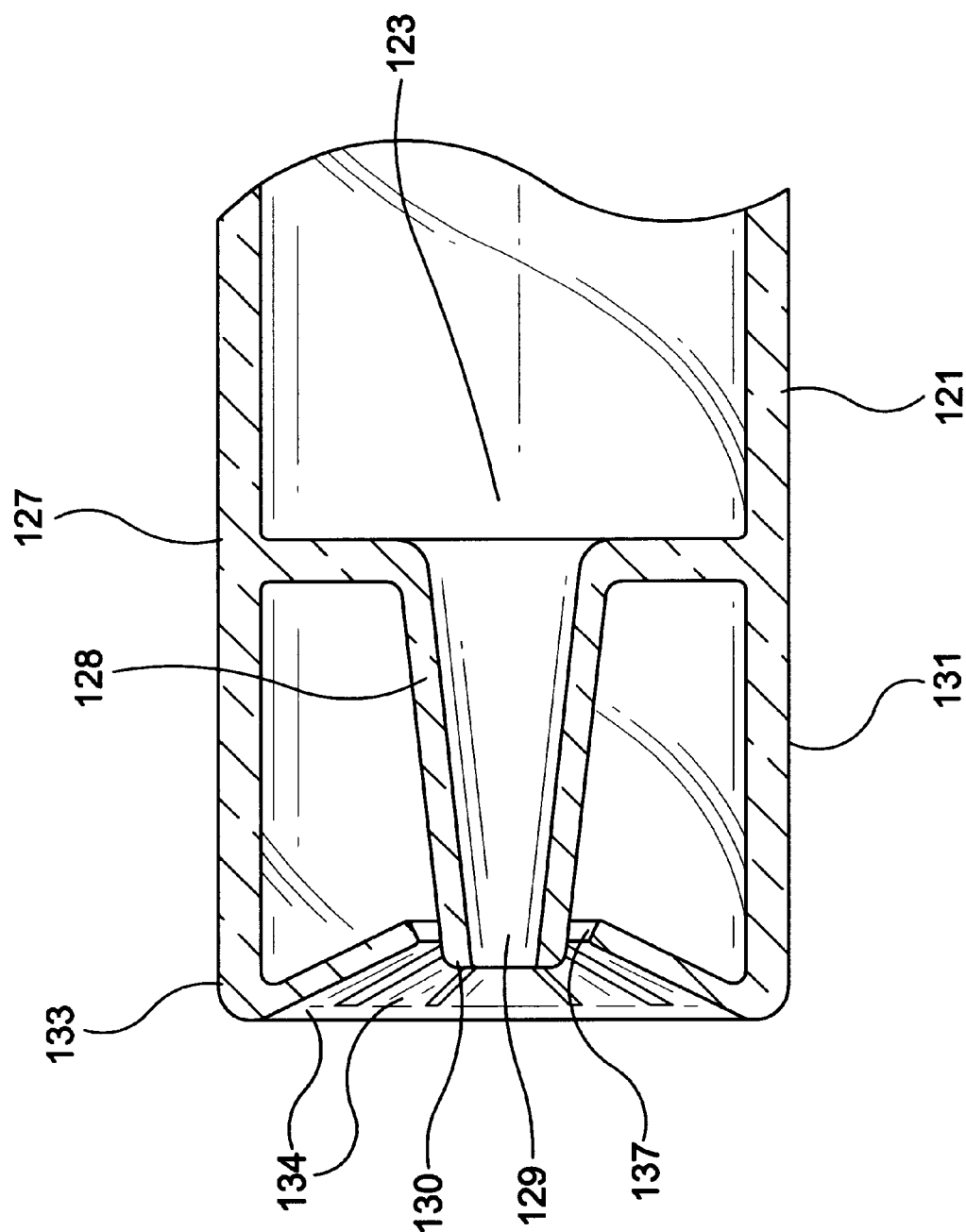
FIG. 8 is an enlarged partial cross-sectional view of an alternative fluid transfer device of the present invention.

FIG. 8 illustrates an alternative embodiment of the present invention. This embodiment is structurally and functionally similar to the embodiment of FIGS. 1–7. In this embodiment, barrel 121 having a chamber 123, a distal end 127 and an elongated frusto-conically shaped tip 128 extending from the distal end and having a passageway 129 in fluid communication with the chamber. A collar 131 preferably surrounds the tip. A plurality of deflectable locking tabs 134 project radially and proximally inward from the collar and toward the tip. Distal ends 137 of the locking tabs define an opening for allowing attachment of a needle assembly to the barrel. In this embodiment, distal end 130 of tip 128 does not extend beyond distal end 133 of the collar as it does in the preferred embodiment of FIGS. 1–7. Having the distal end of the tip extend beyond the distal end of the collar is preferred because it is easier to see the tip of the barrel and to align the barrel tip with the hub cavity for attachment of the needle assembly to the barrel. However, this structure is preferred and not necessary to carry out the present invention. A shorter tip may be desired for various reasons including reducing the amount of material in the barrel.

Figure 9:
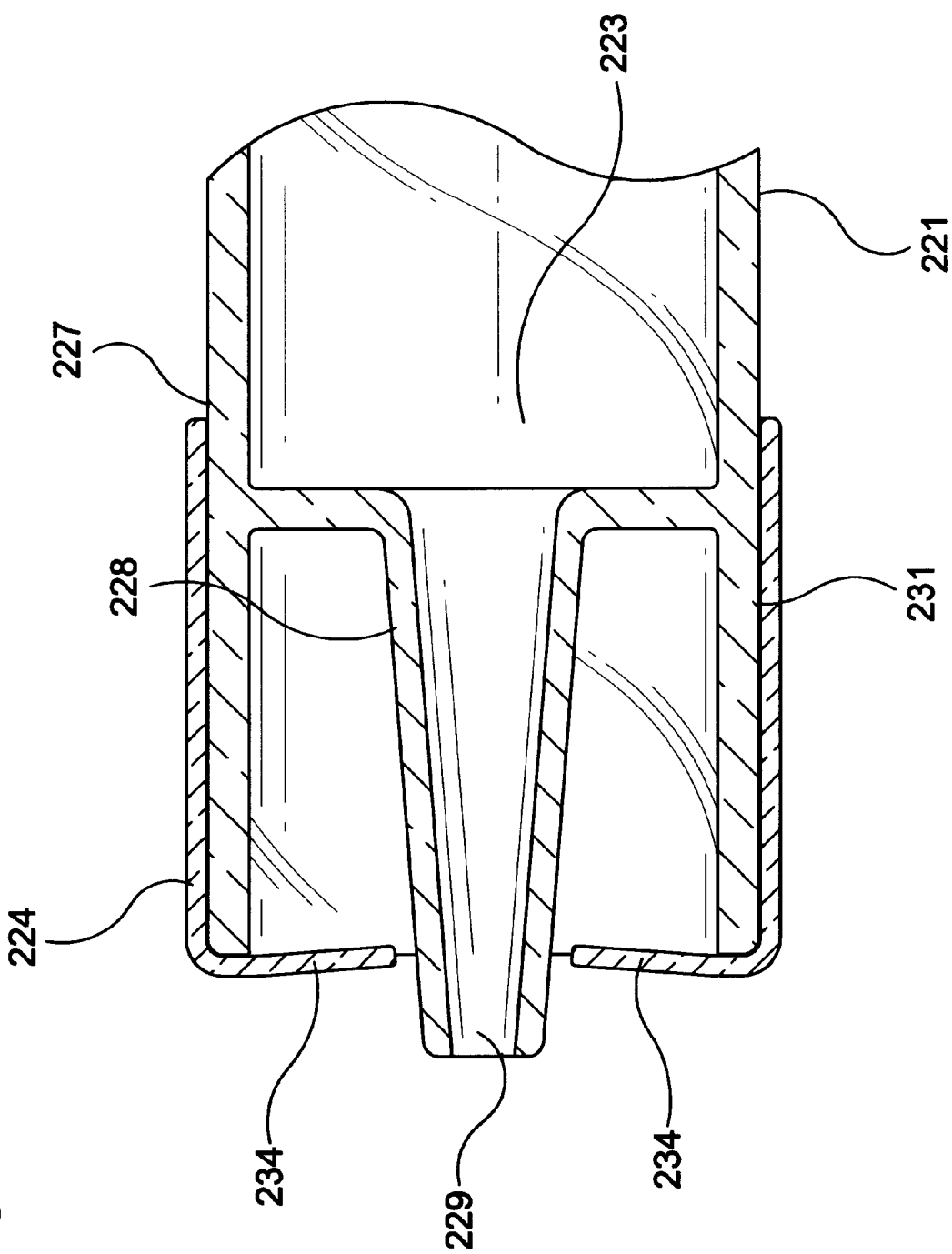
FIG. 9 is an enlarged cross-sectional view of another alternative embodiment of the present invention.

FIG. 9 illustrates another alternative embodiment of the present invention. This embodiment is similar to the embodiment of FIGS. 1–7. In this alternative embodiment, barrel 221 includes an elongated tip 228 extending from distal end 227 of the barrel and having a passageway 229 therethrough in fluid communication with a chamber 223. A collar 231 surrounds the tip. A mounting element 224 is attached to the collar. The mounting element includes at least one locking tab, and in this embodiment, a plurality of locking tabs 234. In this embodiment it is preferred that mounting element 224 and locking tabs 234 are integrally formed of the same material selected form the group of plastic and metal with stainless steel being preferred. The mounting element allows for molding the barrel with a straight collar after which the mounting element can be attached to the distal end of the collar. In this embodiment, deflectable locking tabs are projecting radially inwardly. They are configured so that when the needle assembly is attached to the barrel the hub will force the locking tabs to project radially inwardly and proximally inwardly in an orientation similar to the locking tabs of FIGS. 3 and 8 to prevent the removal of the needle assembly away from the tip after attachment. In this embodiment the locking tabs can also be positioned to project radially inwardly and proximally before the installation of the needle assembly as with the locking tabs of FIGS. 3 and 8. The mounting element can be attached to the collar through various means such as adhesive, welding and/or mechanical means such as press fitting or having locking tabs in the mounting element which allow it to be pressed onto the collar but not removed.

Figure 10:
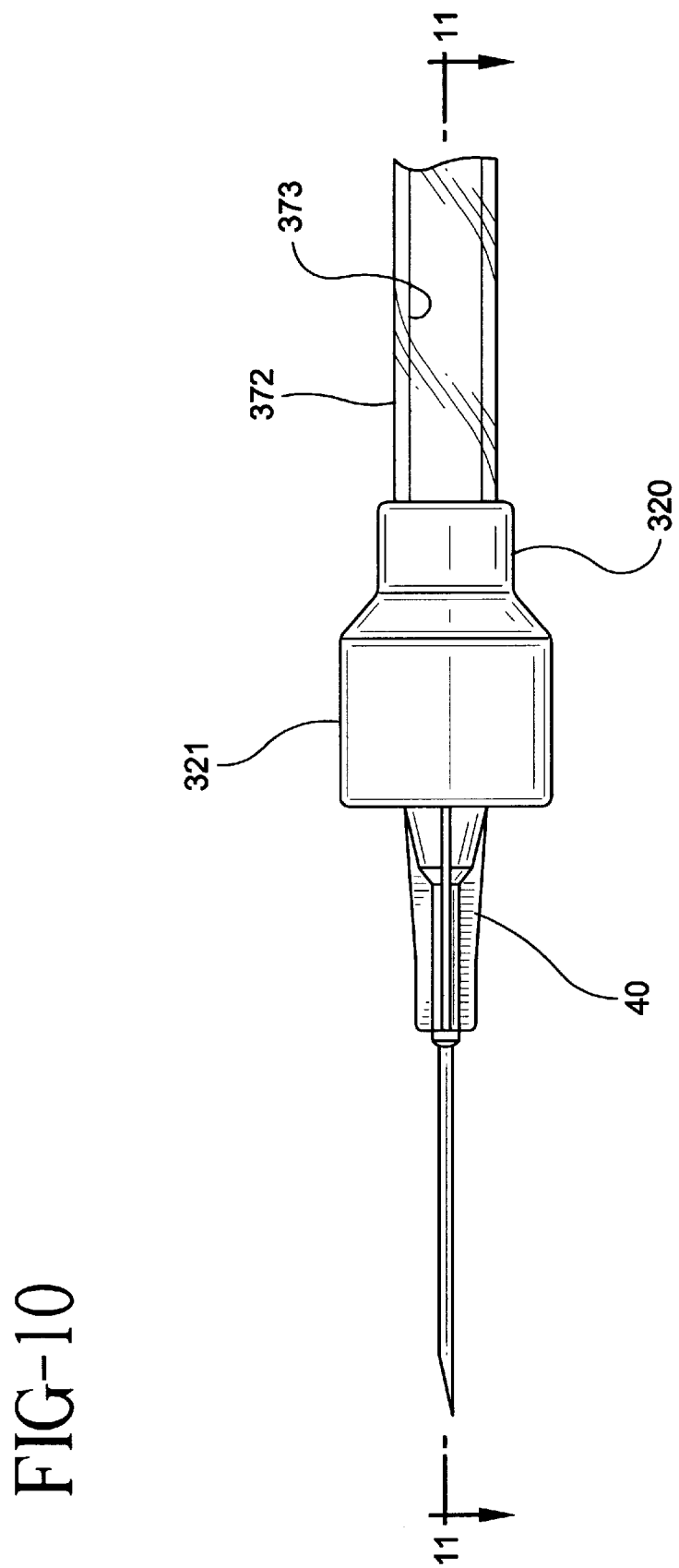
FIG. 10 is an enlarged side-elevational view of an alternative embodiment of the present invention including a flexible tube.
Figure 11:
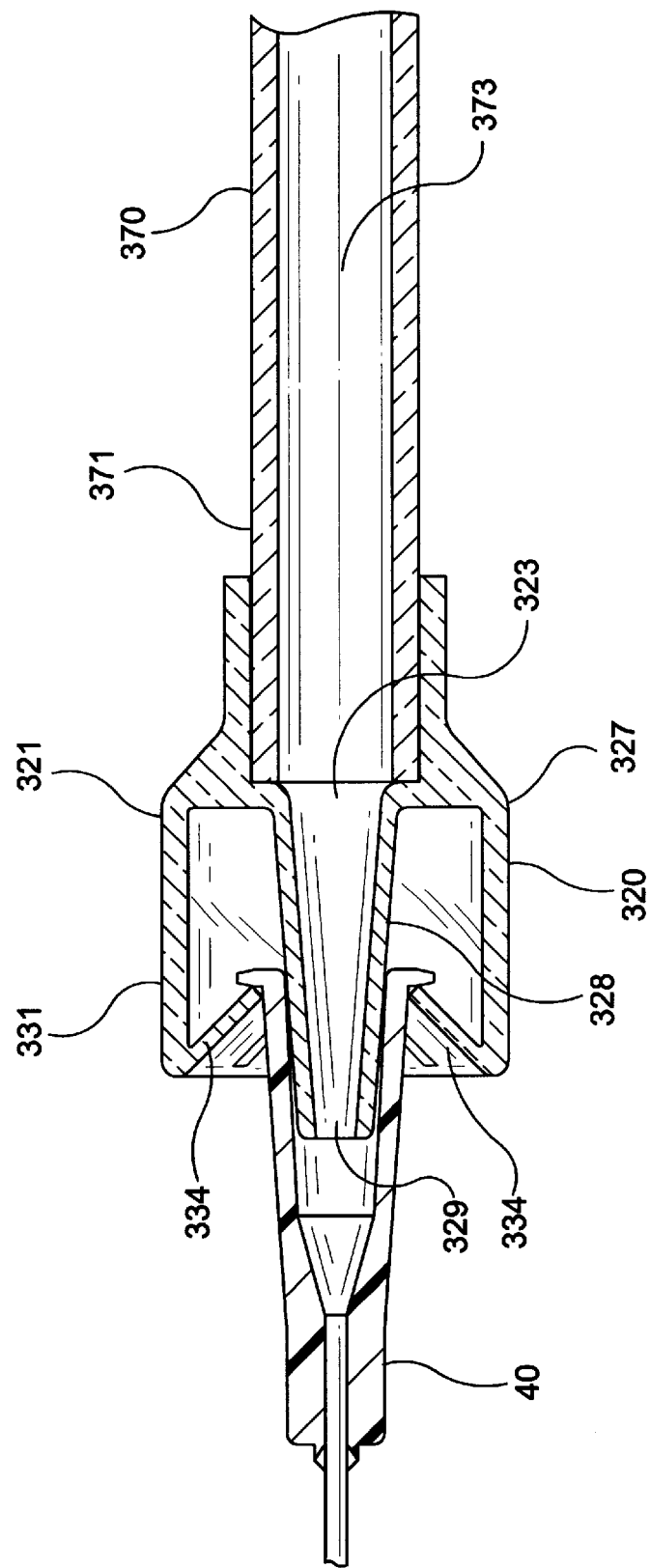
FIG. 11 is an enlarged cross-sectional view of the fluid transfer device of FIG. 10 taken along line 11—11.

FIGS. 10 and 11 illustrate another alternative embodiment of the present invention. This embodiment is illustrated with needle assembly 40 which is identical to the needle assembly of FIG. 6. In this embodiment, fluid transfer device 320 includes a barrel 321 having a chamber 323 and an elongated tip 328 extending from distal end 327 of the barrel and having a passageway 329 therethough in fluid communication with the chamber. A collar 331 preferably surrounds the tip and includes a plurality of deflectable locking tabs 334 projecting radially and proximally inwardly from said collar. A flexible tube 370 having a proximal end, a distal end 371 and a bore 373 therethrough. The distal end of flexible tube 370 is connected to barrel 321 so that bore 373 is in fluid communication with said passageway. Tube 370 can be a catheter or it can be part of an I.V. fluid administration set or various other fluid transfer devices.

Figure 3:
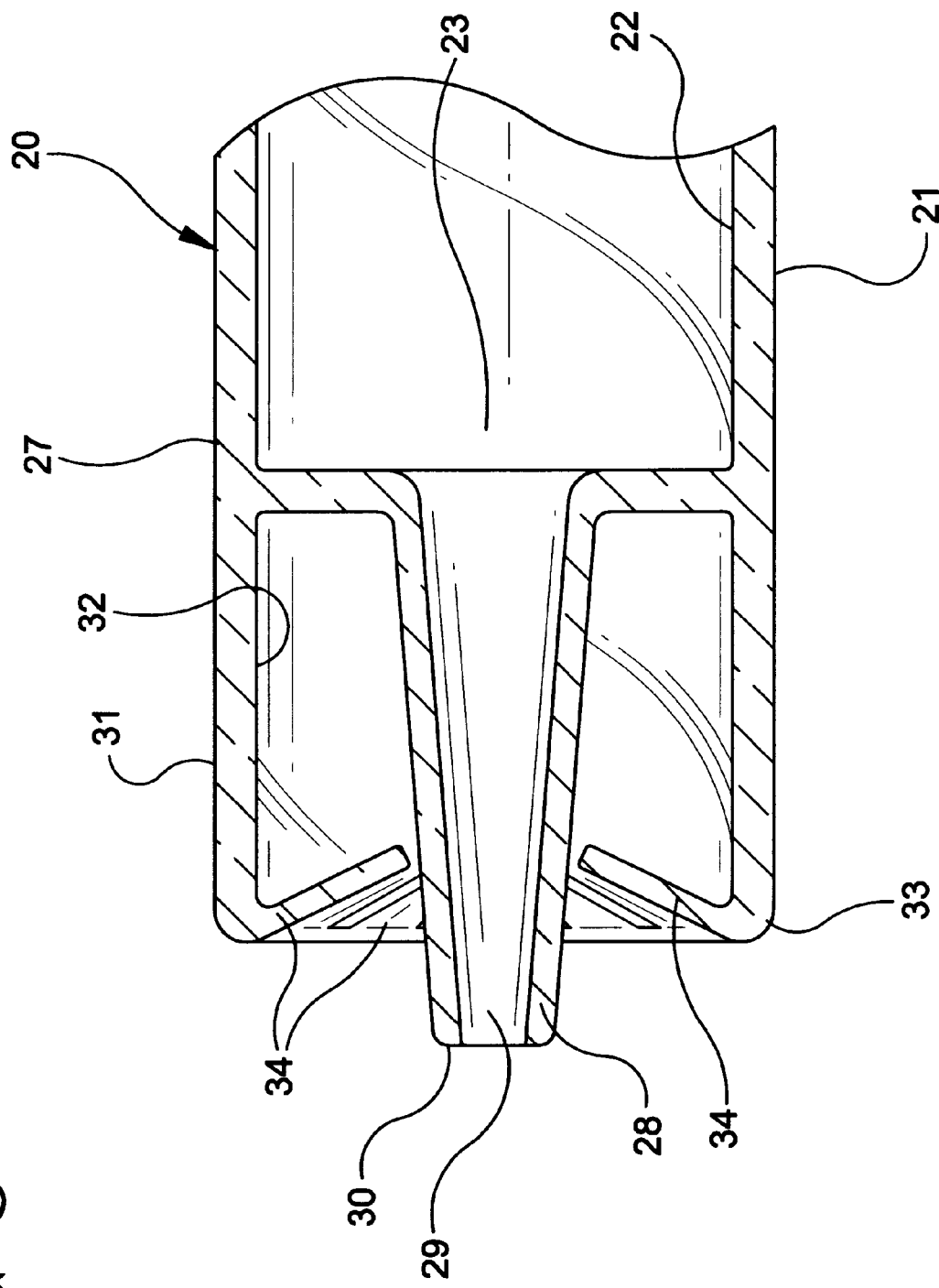
FIG. 3 is an enlarged cross-sectional view of the fluid transfer device of FIG. 2 taken along line 3—3.
Figure 4:
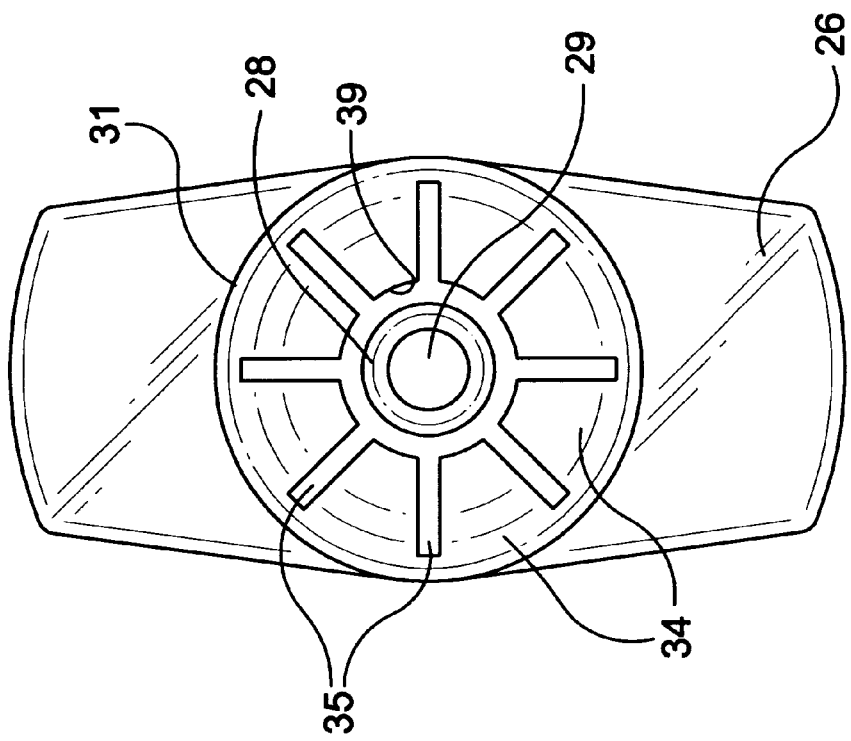
FIG. 4 is a side-elevational view of the left side of the fluid transfer device of FIG. 2.
Figure 12:
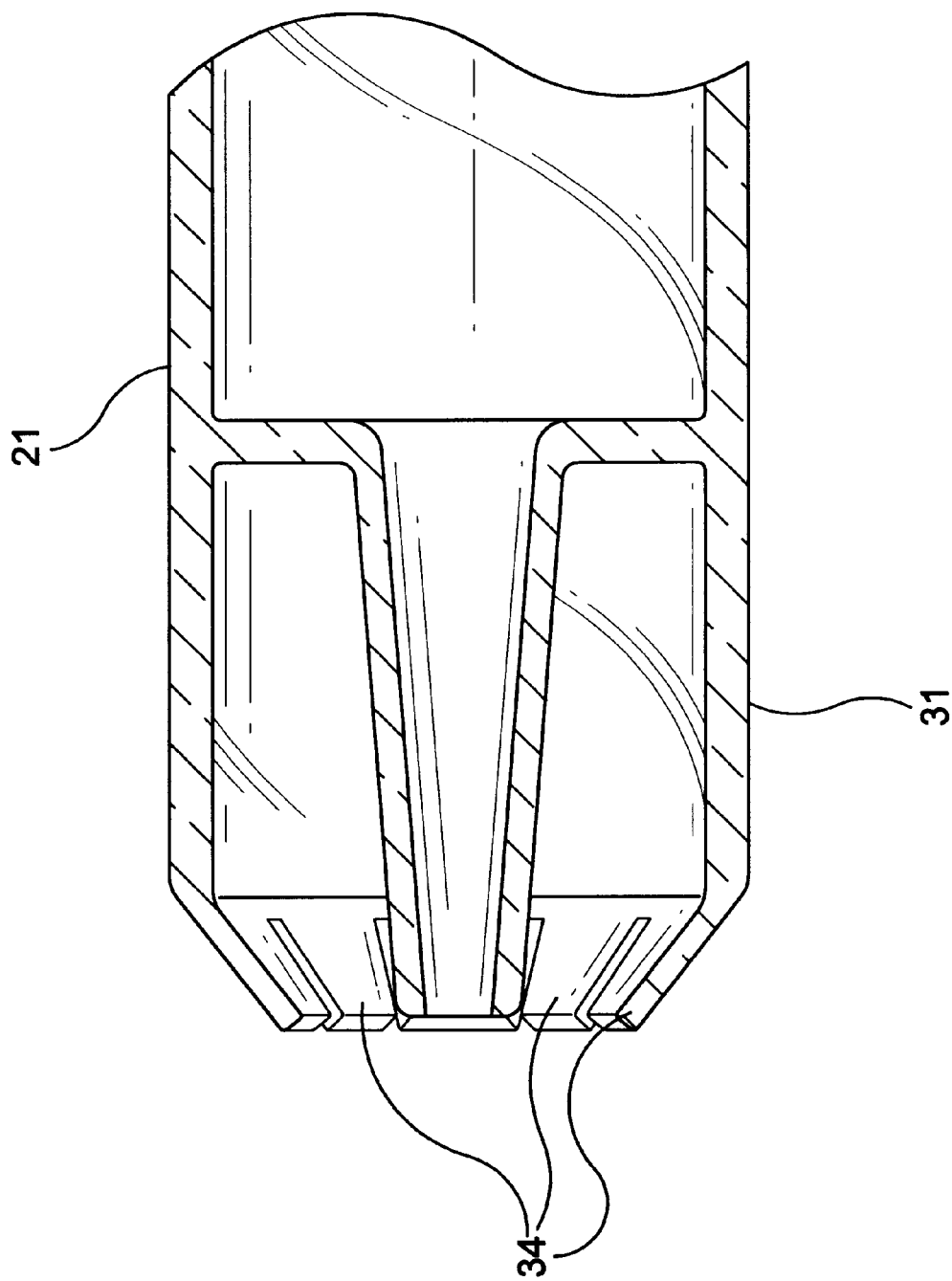
FIG. 12 is an enlarged cross-sectional view illustrating the barrel of the fluid transfer device of FIG. 2 during the manufacturing process.

One method of manufacturing barrel 21 of the present invention is to injection mold the barrel out of thermoplastic material so that deflectable locking tabs 34 are projecting radially and distally inwardly from collar 31 as illustrated in FIG. 12. This configuration allows for easy removal of the barrel from the injection mold. After molding, locking tabs 34 are bent inwardly using force or heat or a combination thereof so that the locking tabs assume a radially and proximally inwardly directed orientation as illustrated in FIG. 3.

Figure 13:
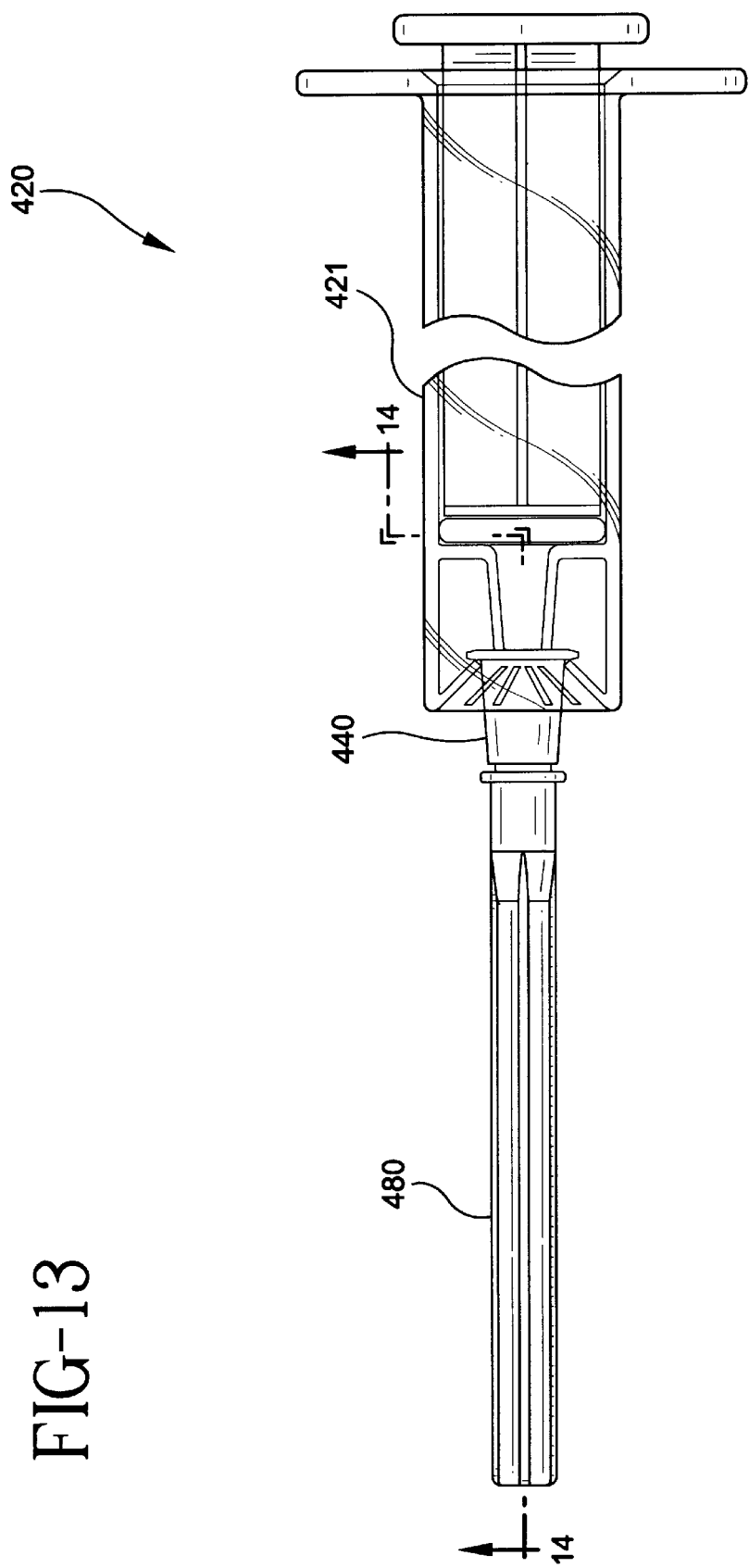
FIG. 13 is a side elevational view of an alternative embodiment of the fluid transfer device of the present invention.
Figure 14:
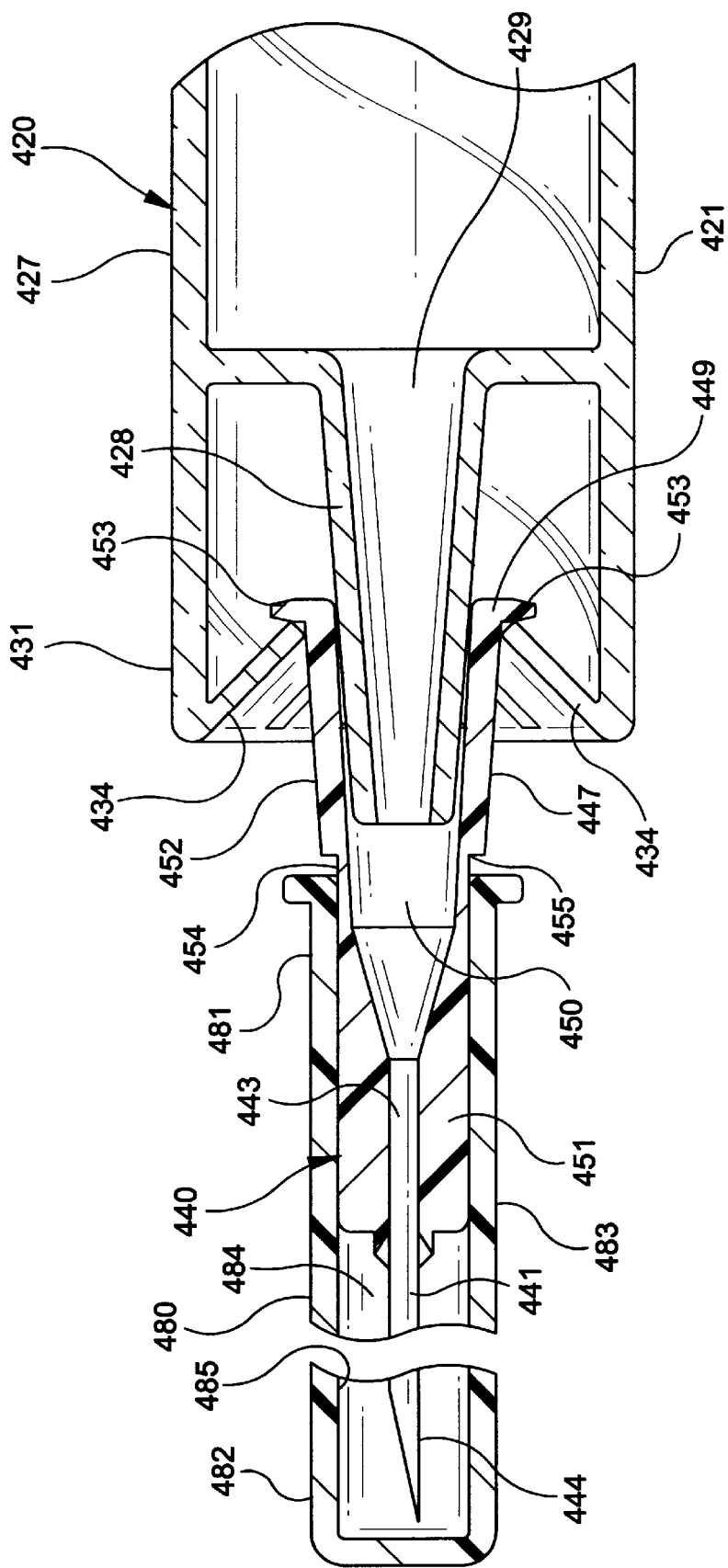
FIG. 14 is an enlarged cross-sectional view of the fluid transfer device of FIG. 13 taken along line 14—14.
Figure 15:
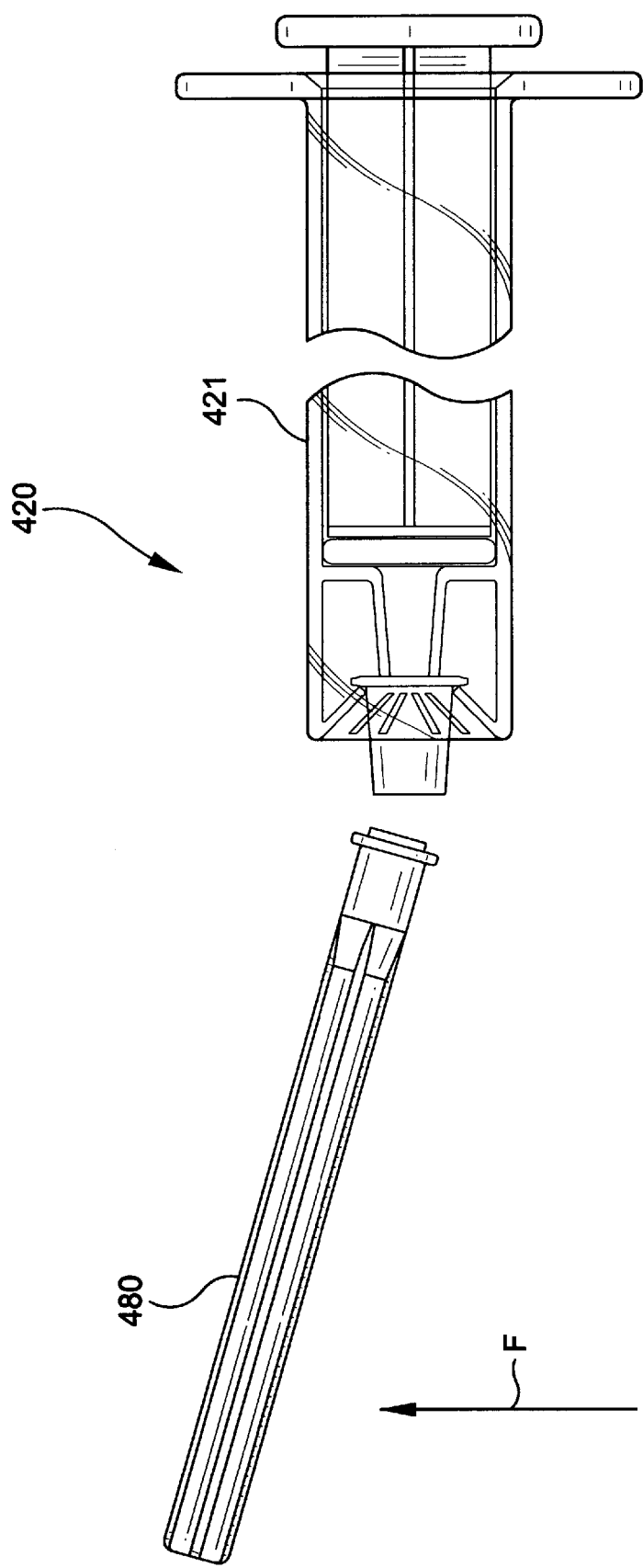
FIG. 15 is a side-elevational view of the fluid transfer device of FIG. 13 illustrating the hub breaking upon application of a bending force.

FIGS. 13–15 illustrate another alternative embodiment of the fluid transfer device of the present invention. This embodiment is similar to the embodiment of FIGS. 1–7. In this embodiment, fluid transfer device 420 includes a barrel 421 having an elongated tip 428 extending from distal end 427 of the barrel and having a passageway 429 therethrough. A collar 431 preferably surrounds the tip and includes a plurality of deflectable locking tabs 434 projecting radially and proximally inwardly from the collar.

A needle assembly 440 includes a cannula 441 having a proximal end 443, a distal end 444 and a lumen therethrough. The needle assembly also includes a hub 447 having an open proximal end 449 with a cavity 450 therein, and a distal end 451 joined to the proximal end 443 of the cannula so that the lumen is in fluid communication with the cavity. Hub 447 also includes outside surface 452. The hub in this embodiment preferably, but not necessarily, includes projections 453 extending radially outwardly from the outside surface of the hub.

A needle shield 480 includes an open proximal end 481, a distal end 482 and a side wall 483 therebetween defining a cavity 484 in the shield. The cavity includes inside surface 485. The shield is removably connected to hub 447 so that distal end 444 of the cannula is contained within cavity 484 of the shield. The removable connection between the shield and the hub is preferably achieved by frictional engagement between inside surface 485 of the shield and outside surface 452 of the hub. There are numerous ways for removably connecting a shield to a hub including a snap-fit arrangement or threaded engagement with the frictional engagement described herein being merely representative of these many possibilities, all of which are within the purview of the present invention. The needle shield is provided to protect the cannula from damage or contamination.

In this embodiment, hub 447 further includes means on the hub between the distal end and the proximal end of the hub for allowing the hub to break upon application of bending force to the hub. In this embodiment, the means for allowing the hub to break includes a fracturable section in the form of annular discontinuity 454 on outside surface 452 of the hub which creates a fracturable section which will cause the hub to break upon application of force F illustrated in FIG. 15. As indicated hereinabove, the fluid transfer device of the present invention provides structure to prevent removal of the needle assembly in the form of one or more locking tabs projecting radially inwardly from the inside surface of the collar which are adapted to engage the outside surface of the hub of the needle assembly. This structure is provided to prevent the improper and undesirable removal of the needle assembly from the barrel. However, an unscrupulous healthcare worker may attempt to apply excessive force to remove the needle assembly by grasping the needle shield and applying a bending force which is generally perpendicular to the longitudinal axis of the cannula in an attempt to cause the hub to overcome the resisting force of the deflectable locking tabs. Since substantial force can be applied it is desirable to have a means on the hub for allowing the hub to break upon the application of a force to the hub which is in excess of the hub forces normally encountered during the known and proper use of the fluid transfer device. In this embodiment, a fracturable section is provided in the form of annular discontinuity 454 on the outside surface of the hub. When force F, illustrated in FIG. 15 is applied the hub will break, preferably in the area of annular discontinuity 454. The discontinuity can, as does in this case, produce an area of reduced cross section in the hub so that this area is the weakest portion of the hub. The discontinuity can also be in the shape of a sharp edge or edges which produce a stress concentration when the hub is subject to bending. In this situation, the result may be obtained without reducing the cross-sectional area significantly or at all. The design would rely on the stress concentration to promote breaking just as scoring of a medication tablet will allow the tablet to break in half along the score line. In this embodiment, sharp annular edge 455 is also provided to promote a stress concentration in the area where the hub is intended to break. Breaking in the area of the fracturable section will cause the cannula to be safely trapped within the needle shield and the needle assembly to be rendered non-reusable. Also, the presence of the proximal end of the hub on the fluid transfer device prevents the addition of a new needle assembly to the device which could allow the undesirable second use of the fluid transfer device. The discontinuity may be on the outside surface of the hub or in the cavity of the hub.

Also, means for allowing the hub to break can be achieved through the use of a brittle material in the entire hub or in the desired breaking area so that bending force will fracture the hub in the area of the brittle material. This result can be achieved using two-part or multi-part molding wherein, for example, the proximal end of the hub is molded of a resilient plastic and the breaking area and the distal end of the hub is molded of a brittle plastic so that the hub will tend to break close to the intersection of the two difference plastics where the largest bending moment on the brittle plastic would be experienced. Since many plastics can be formulated to exhibit a wide variety of properties from very ductile to very brittle, the choice of a hub material is quite broad. When using two-part molding, the plastics should be chosen for their properties and for their compatibility with each other at the intersection of the two plastic materials in the hub. Polypropylene, polyethylene, styrene and polycarbonate are preferred plastic materials for the hub. Styrene and polycarbonate can be formulated to be very brittle and/or sensitive to surface discontinuities and can be used for the entire hub for the part of the hub where the fracture is desired. All of the above-described materials and structures are within the purview of the present invention.

It is an important feature of the present embodiment that it provides two means for preventing the unwanted removal of the needle assembly from the fluid transfer device. The first is the resisting action of the deflectable locking tab or tabs against the outside surface of the hub and the second is the fracturable section of the hub which will cause the hub to break upon the application of excessive force used in an attempt to overcome the action of the deflectable locking tabs.

Figure 16:
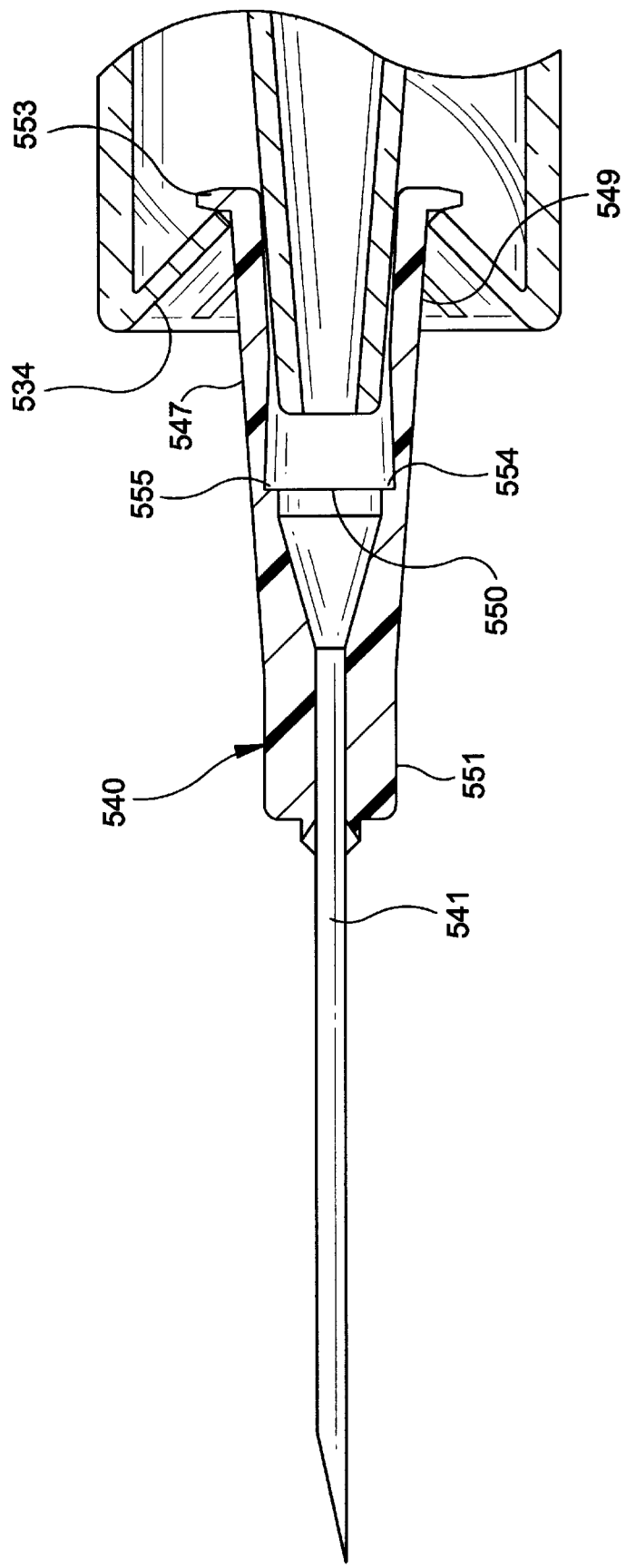
FIG. 16 is an enlarged cross-sectional view of another alternative fluid transfer device.
Figure 17:
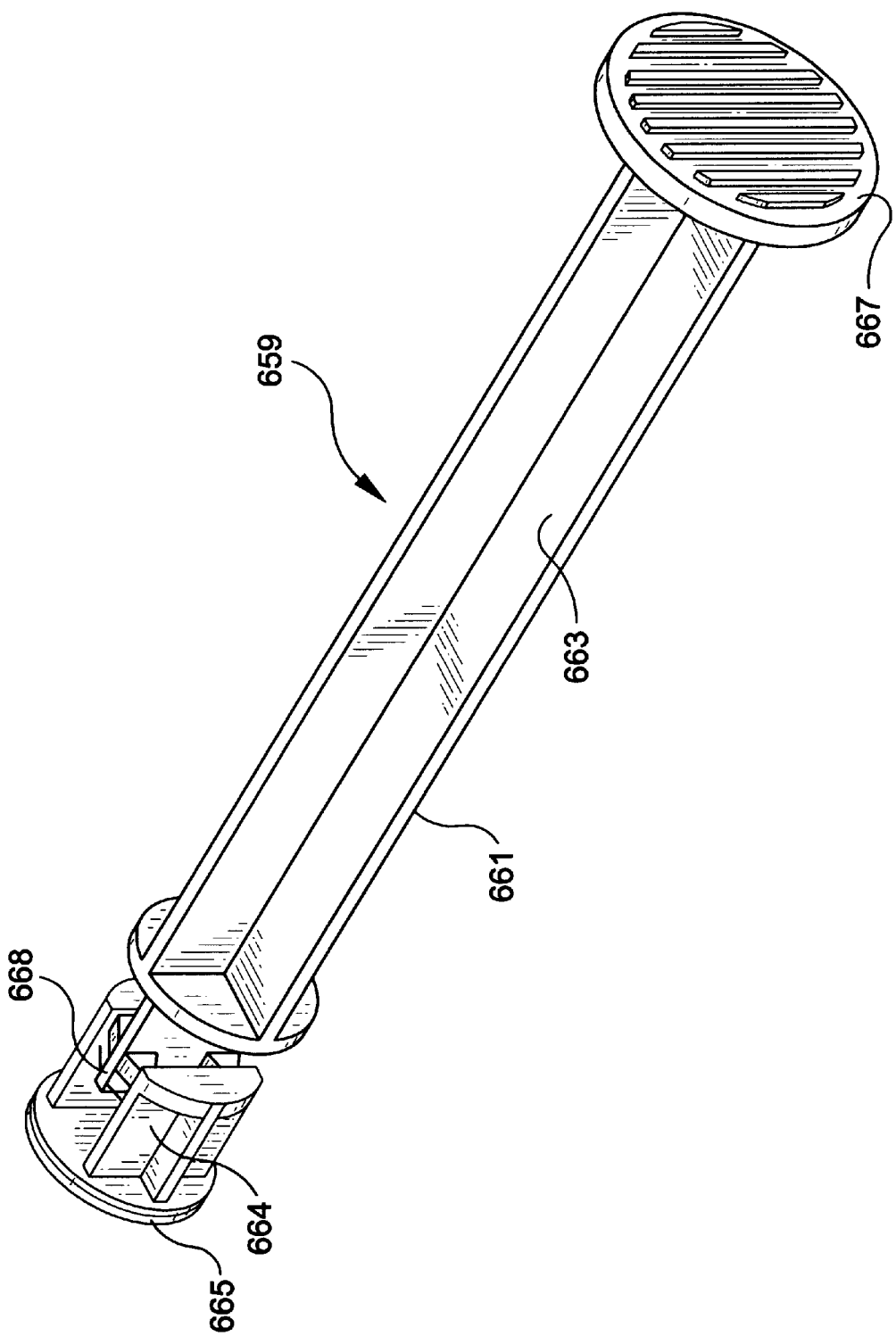
FIG. 17 is a perspective view of the plunger of an alternative embodiment of the present invention having a distal portion and a proximal portion connected by a breakable connection.
Figure 18:
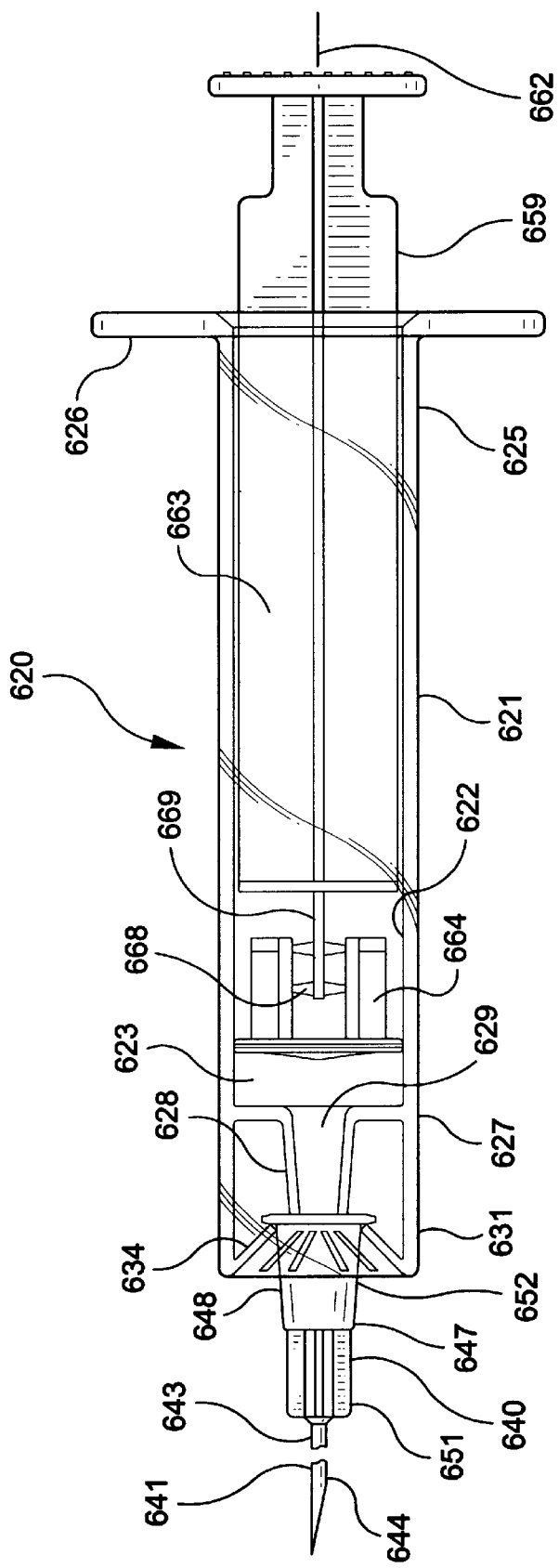
FIG. 18 is a side elevation view of a syringe assembly using the plunger of FIG. 17.
Figure 19:
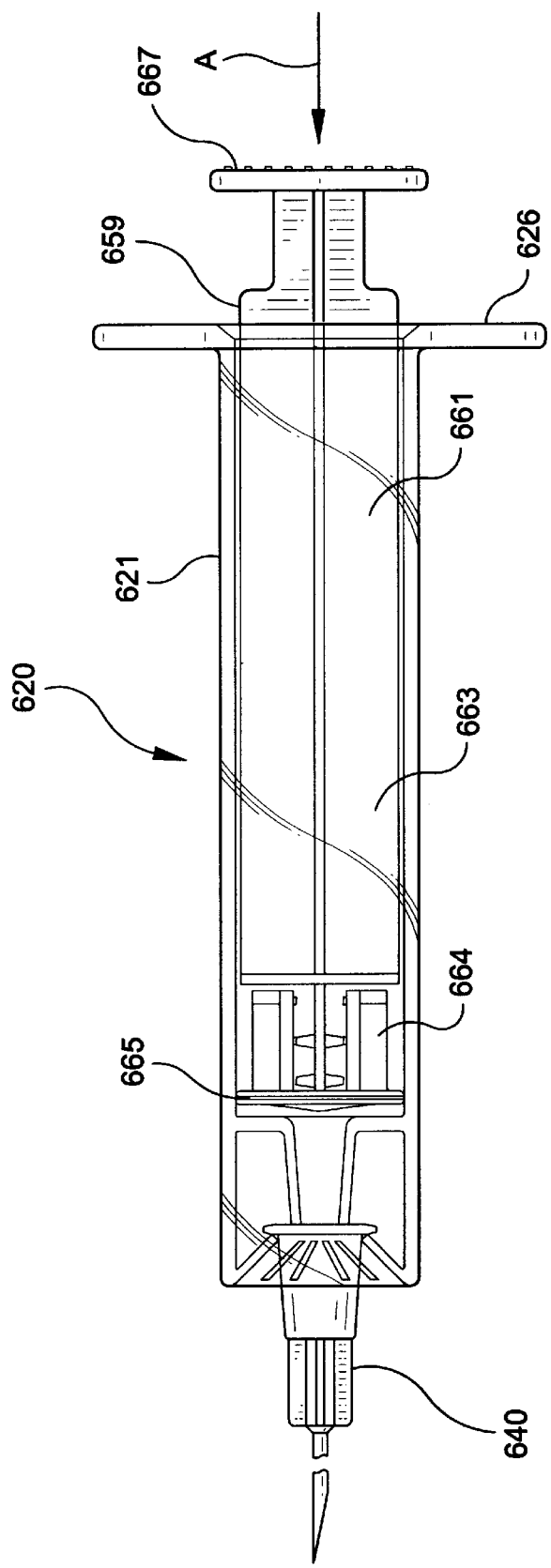
FIG. 19 is a side elevational view of the syringe of FIG. 18 illustrated with a force being applied to break the connection to the proximal and distal ends of the plunger rod.

FIG. 16 illustrates another alternate embodiment of the fluid delivery device of the present invention. In this embodiment, needle assembly 540 includes a cannula 541 and a hub 547. The hub includes open proximal end 549 with a cavity 550 therein and a distal end 551. Needle assembly 540 further includes a fracturable section between the proximal end and the distal end of the hub for allowing the hub to break upon application of a bending force to the hub. In this embodiment, the fracturable section includes an annular discontinuity 554 in cavity 550. Annular discontinuity 554 also preferably includes sharp annular stress concentrating edge 555 to help promote breakage in the area of the discontinuity. This embodiment, like the embodiment of FIGS. 13–15 provides two-step protection against the undesirable removal of the needle assembly from the fluid transfer device. The first protection is offered by the interaction of flexible locking tabs 534 to hold the hub in its position on projection 553. The second protection is the fracturable section for allowing the hub to break upon the application of bending forces on the hub in excess of those experienced during normal proper use of the fluid transfer device.

FIGS. 17–20 illustrate another alternative embodiment of the present invention. In this embodiment the fluid delivery device is syringe 620 comprising barrel 621 having a fluid chamber 623, a proximal end 625, a distal end 627 and an elongated tip 628 extending from the distal end and having a passageway 629 therethrough in fluid communication with the chamber. A collar 631 surrounds the tip. At least one deflectable locking tab projects radially inwardly from the collar. In this embodiment, there are a preferably a plurality of locking tabs 634.

A needle assembly 640 includes a cannula 641 having a proximal end 643, a distal end 644 and a lumen therethrough. A hub 647 includes an open proximal end 649 with a cavity therein, and a distal end 651 joined to the proximal end of the cannula so that the lumen is in fluid communication with the cavity of the hub. The hub further includes an outside surface 652. The needle assembly is connected to the barrel so that the elongated tip of the barrel is in the cavity of the hub and the outside surface of the hub is adjacent to the one or more locking tabs so that the locking tabs prevent removal of the needle assembly from the barrel through contact between the locking tab and the outside surface of the hub. Locking tabs are configured to allow the assembly of the needle assembly to the barrel through axial motion of the hub toward the barrel.

A plunger 659 includes an elongated plunger rod 661 having a longitudinal axis 662, a proximal portion 663 and a distal portion 664 connected by a breakable connection 668. Distal portion 664 includes a stopper 665 slidably positioned in fluid-tight engagement with an inside surface 622 of the chamber for drawing fluid in and out of the chamber by movement of the plunger relative to the barrel. Stopper 665 may be a separate element connected to distal portion 664 or it may be integrally molded with the distal portion in a one-piece plastic construction. Separate stoppers are preferably made of elastomeric material such as natural rubber, synthetic rubber, thermoplastic elastomers and combinations thereof. Breakable connection 668 is strong enough to hold proximal portion 663 and distal portion 664 together during normal use of the syringe and is breakable upon application of additional force to the proximal portion.

Proximal end 663 further includes a flange 667 for applying forces to move the plunger rod with respect to the barrel and for breaking the breakable connection. A flange 626 is also provided at the proximal end of the barrel to facilitate handling of the syringe and for applying forces to the plunger using a one-handed procedure as will be explained in more detail hereinafter.

In this embodiment, there are a plurality of breakable connections connecting proximal portion 663 and distal portion 664. Specifically, proximal portion 663 includes a distal projection 669 having at least one transverse protuberance projecting therefrom. In this preferred embodiment, there are four transverse protuberances 670. The protuberances are connected to distal portion 664 and the breakable connection is on the protuberance. In this preferred embodiment breakable connection 671 is on the distal end of the protuberance. The distal projection may be circularly shaped and fit into a cylindrically shaped recess in the distal portion. With this structure a single protuberance extending up to 360 degrees may be used. The structure may also be reversed so that the projection extends proximally from the distal portion toward the proximal portion.

In this preferred embodiment, proximal portion 663 and distal portion 664 and the breakable connections are integrally molded of plastic material. A wide variety of plastic materials are suitable for molding the plunger with polystyrene, polypropylene and polyethylene being preferred. It is important to control the modulus of elasticity of material selected for the transverse protuberances which are part of the breakable connection between the proximal portion and the distal portion of the plunger rod. The breakable connection must break or fail before the proximal portion of the plunger bottoms out or makes contact with the distal portion of the plunger. If the modulus is too high the break will occur too easily, causing premature breakage. If the modulus is too low the breakable connection may not break before the proximal portion and the distal portion contact each other. Also, careful controlling of the modulus will allow use of materials such as polypropylene which would not normally be used to form a breakable connection. It is preferred to have a modulus of elasticity be within the range of about 800 MPa to 4000 MPa.

The breakable connections can be anywhere along the protuberance, at its proximal end, its distal end, or in between, depending on, among other things, the geometry of the protuberance. A breakable connection can also be made by connecting the protuberance to the distal end or to the proximal end using a frangible adhesive. The protuberance may be very short and made entirely of adhesive or frangible material. The connection can also be made using a shear pin passing through the distal projection 669 and distal portion 664. The shear pin may be made of plastic with one or more notches or stress risers suitably placed to cause breaking at the desired force levels. The breakable connection between the proximal portion and the distal portion may also be accomplished by using a snap-fit arrangement a portion of which is damaged or broken when the desired force is applied. In this latter situation, the distal portion and the proximal portion can be individually molded and snapped together during the assembly process.

In use, the syringe of this embodiment can be filled from a vial, ampoule or other suitable container using known safe procedures. An important advantage of the present embodiment is that the plunger can be moved back and forth along the barrel as many times as necessary to properly fill the syringe barrel. For example, the syringe barrel may be filled with sterile water and then the sterile water can be injected into a vial containing a lyophilized medication which is then drawn back into the syringe barrel. Many single-use syringes in the prior art only allow one proximal motion of the plunger with respect to the barrel. With these single-use syringes, once the plunger is moved in a distal direction with respect to the barrel it can no longer be withdrawn. Therefore, mixing sterile water and a lyophilized medication as described above is not possible.

Another advantage of the present embodiment is that the plunger can be moved to its distal-most position with respect to the barrel and then moved proximally. Some prior art single use syringes automatically lock the plunger to the barrel when the plunger is moved to its distal-most position. These prior art designs can lead to unintentional locking of the plunger before use and can compromise filling and mixing procedures.

Figure 20:
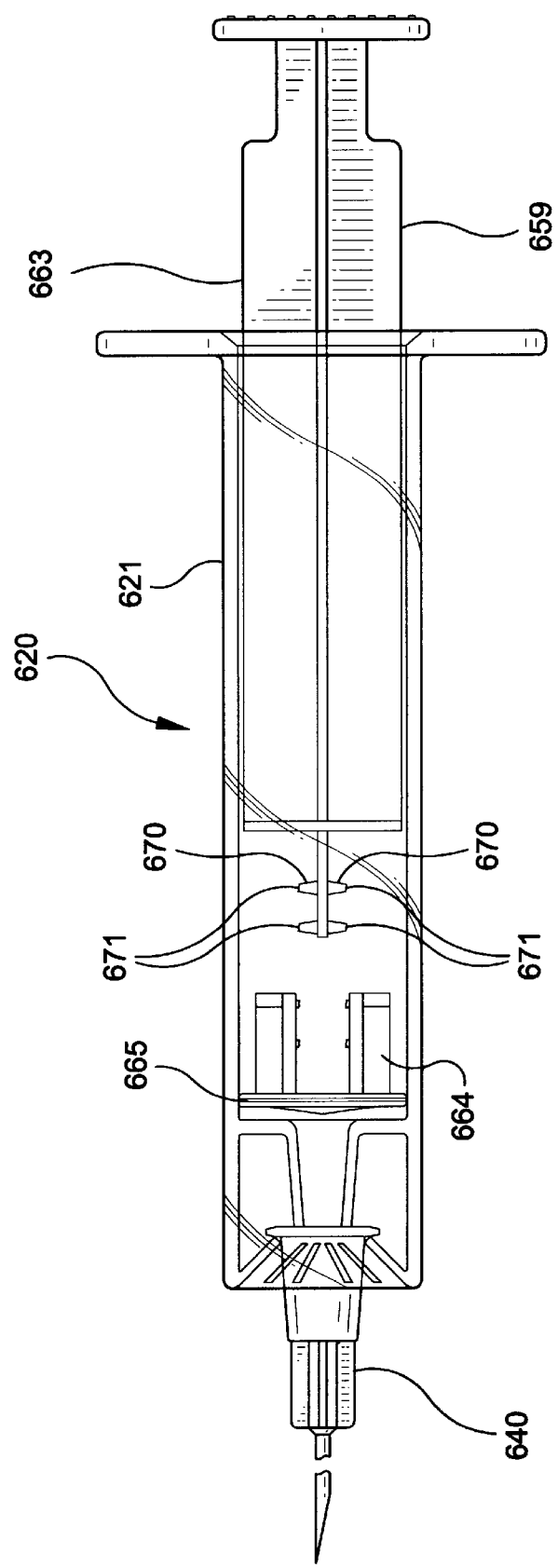
FIG. 20 is a side elevational view of the syringe of FIG. 19 illustrating the separated proximal and distal ends of the plunger rod.

The liquid in the barrel can now be injected into a patient or delivered in another suitable manner such as through the pierceable septum of a catheter connector. Upon completion of the injection the user can apply an additional force indicated as A in FIG. 19, to the proximal portion. In this embodiment the breakable connections are broken by the application of a distally directed force A applied to the proximal end of the proximal portion along longitudinal axis 662. Force A is sufficient to break the breakable connections which causes the plunger rod to separate into two or more unusable pieces. In this enablement the proximal portion and the distal portion are separated as illustrated in FIG. 20.

An important advantage of the present invention is that the breakable connection can be broken using any one-handed technique, for example, pressing on plunger rod flange 667 in direction A with the thumb of one hand while holding the syringe barrel and/or the syringe barrel flange with some or all of the remaining fingers. This is desirable over a two-handed technique wherein the barrel must be held by one hand and the plunger by another to carry out a breaking manipulation such as bending or twisting.

The embodiment of FIGS. 17–20 is a significant advance over single-use syringes of the prior art. In particular, it allows multiple strokes of the plunger with respect to the barrel without automatically locking and rendering the syringe unusable. This design also allows the plunger to move to its distal-most position inside the barrel without automatically locking the plunger to the barrel. It also provides two mechanisms to prevent or discourage re-use. First, the needle assembly is securely locked in place so that it cannot be removed from the barrel for improper re-use. Second, the plunger is breakable so that its proximal and distal ends are separated and the syringe, with the needle locked in place, can no longer be used to inject medication. Further, the plunger breaking feature is accomplished by a simple onehanded procedure.

Figure 21:
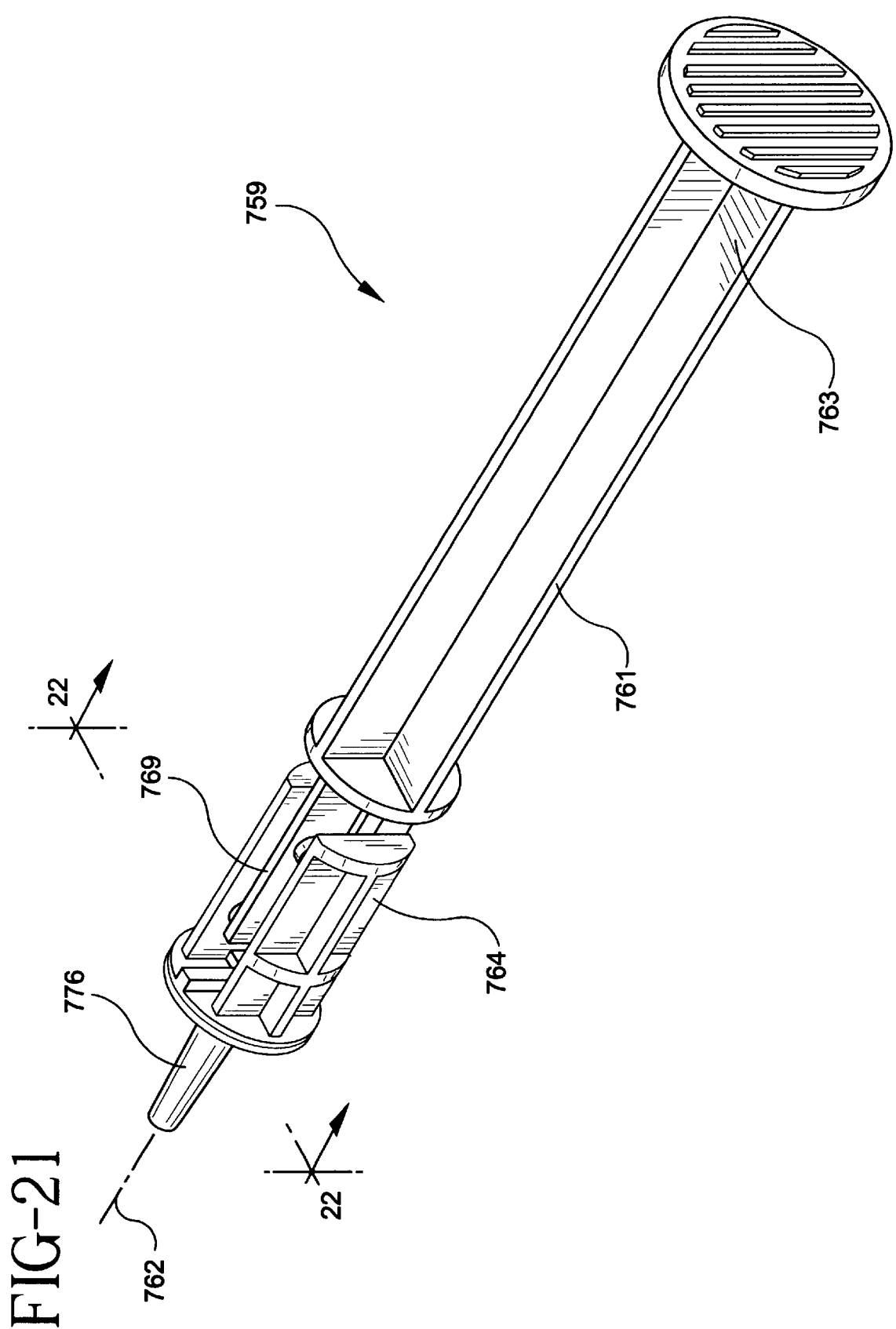
FIG. 21 is a perspective view of the plunger of an alternative embodiment of the present invention.
Figure 22:
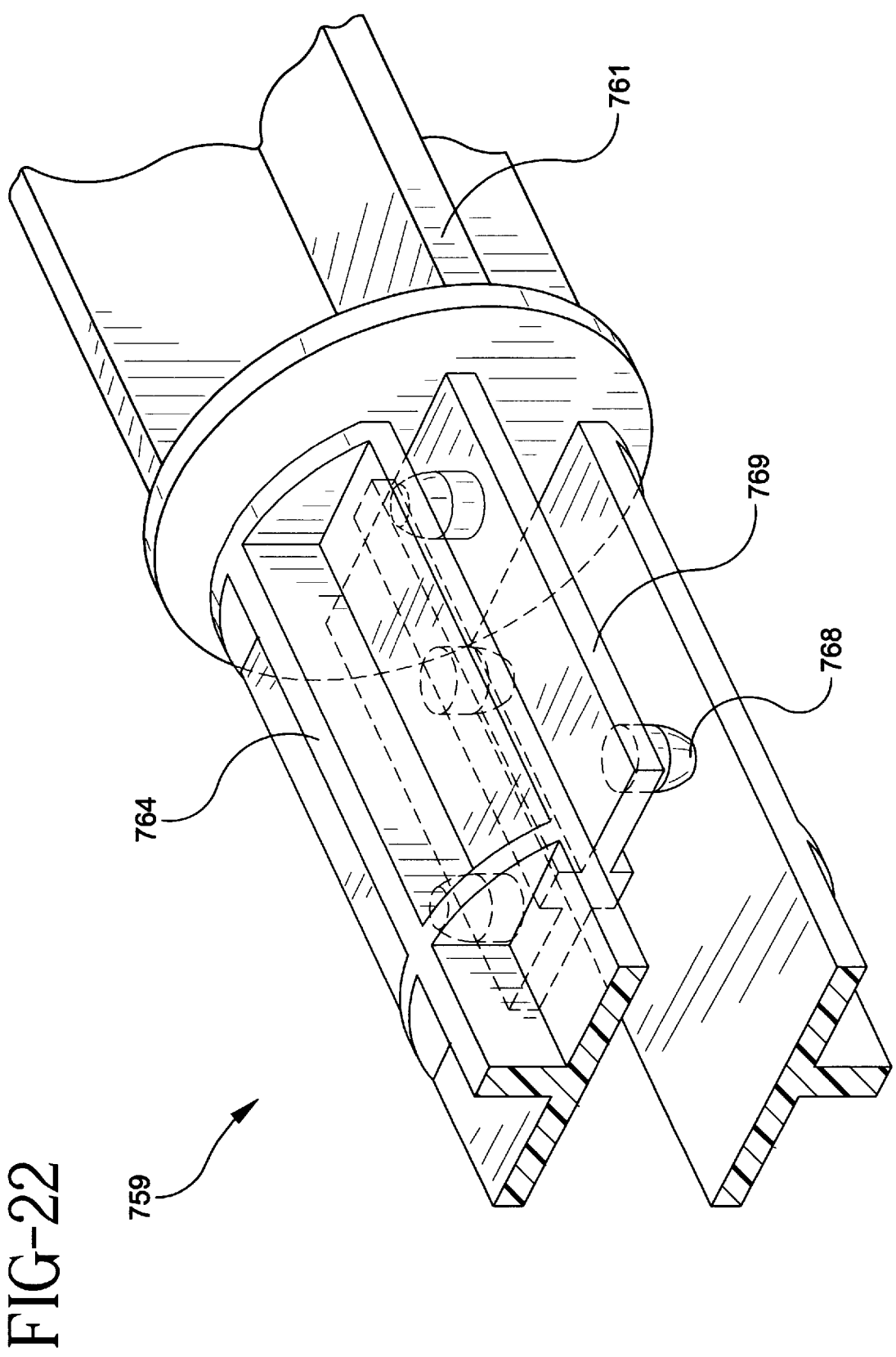
FIG. 22 is an enlarged partial cross-sectional view of the plunger of FIG. 21 taken along lines 22—22.
Figure 23:
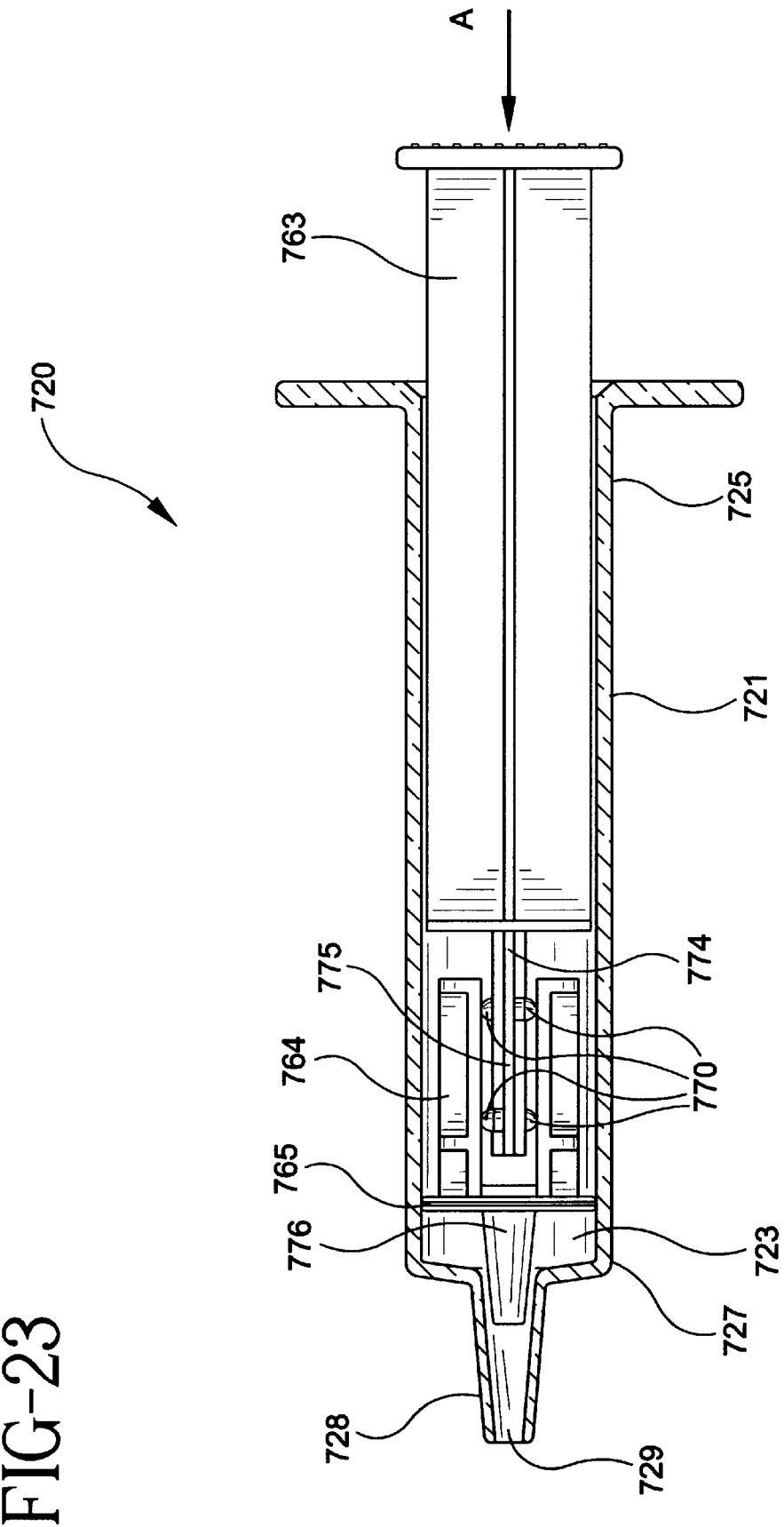
FIG. 23 is a partially cross-sectional side elevational view of a syringe assembly using the plunger of FIG. 21.

FIGS. 21–23 illustrate another alternative embodiment of the present invention. In this embodiment, the fluid delivery device is a syringe 720 comprising a barrel 721 having a fluid chamber 723, a proximal end 725, a distal end 727 and an elongated tip 728 extending from the distal end and having a passageway 729 therethrough in fluid communication with the chamber.

A plunger 759 includes an elongated plunger rod 761 having a longitudinal axis 762, a proximal portion 763 and a distal portion 764 connected by a breakable connection 768. It is preferred that either proximal portion 763 or distal portion 764 include an axial projection. In this embodiment an axial projection 769 is on proximal portion 763. Axial projection 769 includes at least one transverse protuberance projecting therefrom. In this preferred embodiment, there are four transverse protuberances 770. The protuberances are connected to distal portion 764 and the breakable connection is on the protuberances. The transverse protuberances project from opposite sides of the axial projection. Also, in this embodiment, two of transverse protuberances 770 project in substantially the opposite direction than the other two transverse protuberances 770. It is preferable that proximal portion 763 and distal portion 764 and the transverse protuberances 770 which include breakable connections are integrally molded of plastic material.

Plunger 759 in this embodiment functions similarly to plunger 659 in the embodiments of FIGS. 17–20.

Distal portion 764 includes a stopper 765 slidably positioned in fluid-tight engagement with an inside surface of chamber 723 for drawing fluid into and out of the chamber by movement of plunger 759 relative to barrel 721. The breakable connection is strong enough to hold the proximal portion and the distal portion together during normal use of the syringe and breakable upon application of an additional force applied to the proximal portion along the longitudinal axis such as distally directed force A in FIG. 23. It is preferred that the additional distally directed force required to break the breakable connection be within the range of about 2.2 kg to 6.8 kg (5 lbs. to 15 lbs.). The proper force depends on various dimensions of the syringe barrel and plunger, the viscosity of the liquid being delivered and the mechanical and hydraulic forces encountered by the filling and delivery process. If the breakable connection is too weak the proximal and distal portions will separate during normal use of the syringe and if the force required to break the breakable connection is too high the user may not be able to easily break the breakable connection as intended. In this embodiment axial projection 769 is planar shaped having two opposed side walls 774 and 775 with at least one transverse protuberance projecting from each of the side walls. In this embodiment, there are two transverse protuberances projecting from each side wall. This structure because of the planar axial projection and the diagonal positioning of the transverse protuberances is preferred because it creates a secure linkage between the proximal portion and the distal portion and it is strong with respect to rotational movement or rotational forces applied to the plunger and weaker with respect to axial forces applied to the plunger so that rotational forces should not break the breakable connection.

This embodiment further includes distally directed projection 776 on the distal portion for displacing fluid in passageway 729 when the plunger is positioned distally with respect to the barrel. This is an important feature of this embodiment because it saves medication that might otherwise remain in the passageway after the injection process was completed. In an immunization program involving millions of syringes, the amount of medication saved by the cooperative relationship between the distally directed projection and the passageway can be substantial. Even a four percent improvement can result in a free dose for every twenty-five syringes used.

Figure 24:
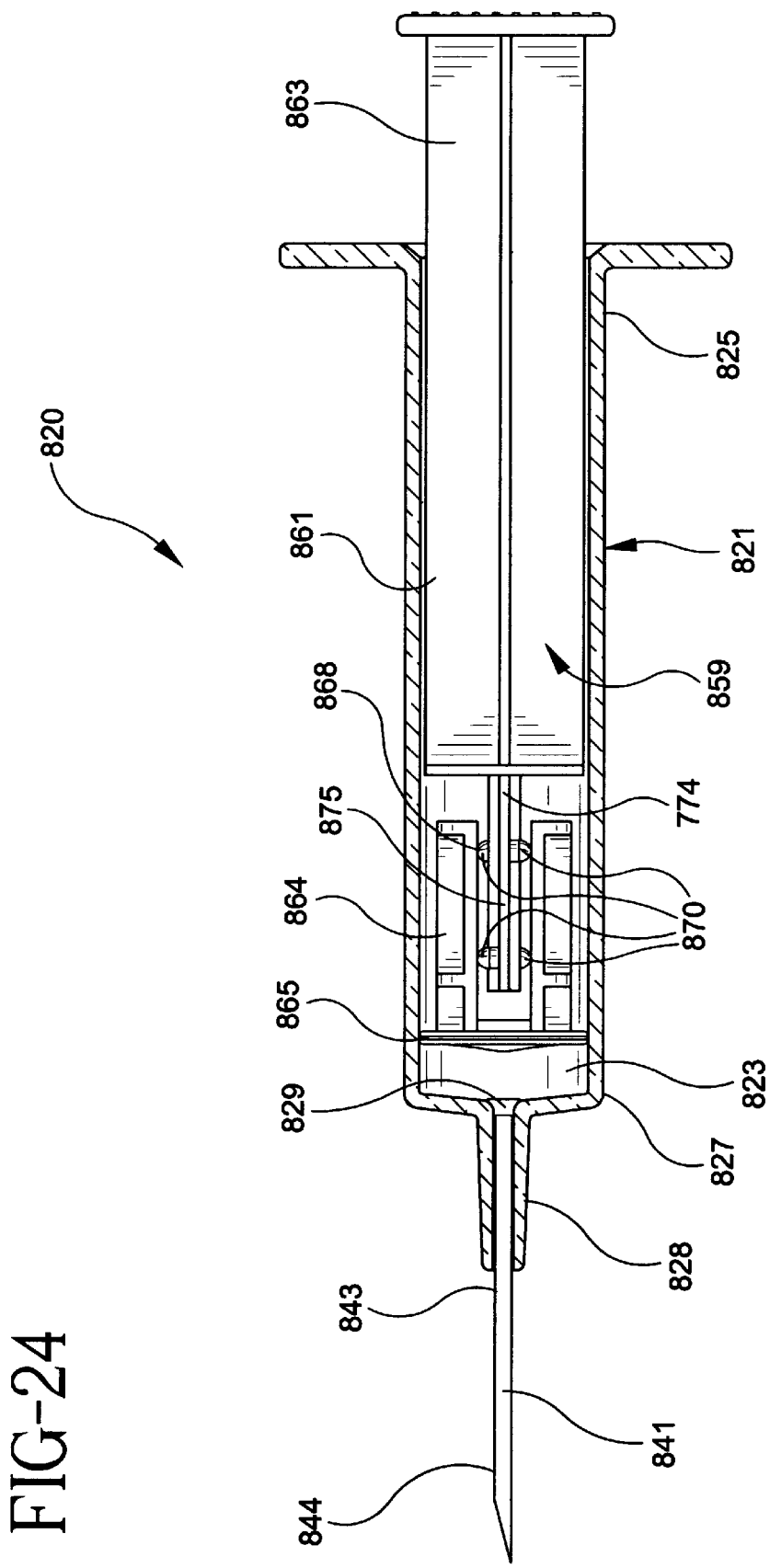
FIG. 24 is a partially cross-sectional side elevational view of an alternative syringe assembly embodiment of the present invention having a cannula attached directly to the syringe barrel.

FIG. 24 illustrates another alternative embodiment of the present invention. In this embodiment the fluid delivery device is a syringe 820 which functions similarly to the syringe of the embodiment of FIGS. 17–20. The syringe includes a barrel 821 having a fluid chamber 823, a proximal end 825, a distal end 827 and an elongated tip 828 extending from the distal end and having a passageway 829 therethrough in fluid communication with the chamber. The syringe further includes a cannula 841 having a proximal end 843, a distal end 844 and a lumen therethrough. The proximal end of the cannula is joined to elongated tip 828 so that the lumen is in fluid communication with passageway 829. A plunger 859 having an elongated plunger rod 861, a proximal portion 863 and a distal portion 864 connected by a breakable connection 868.

Cannula 841 is preferably permanently connected to the barrel so that it is not replaceable or removable during normal use. There are many ways to connect the cannula to a barrel including adhesives, such as epoxy. An advantage of this embodiment is that it can be configured to save medication from being wasted and, more importantly, when the breakable connection is broken the plunger is no longer usable and the needle cannot be removed from the syringe to be used again in an undesirable manner.

Figure 25:
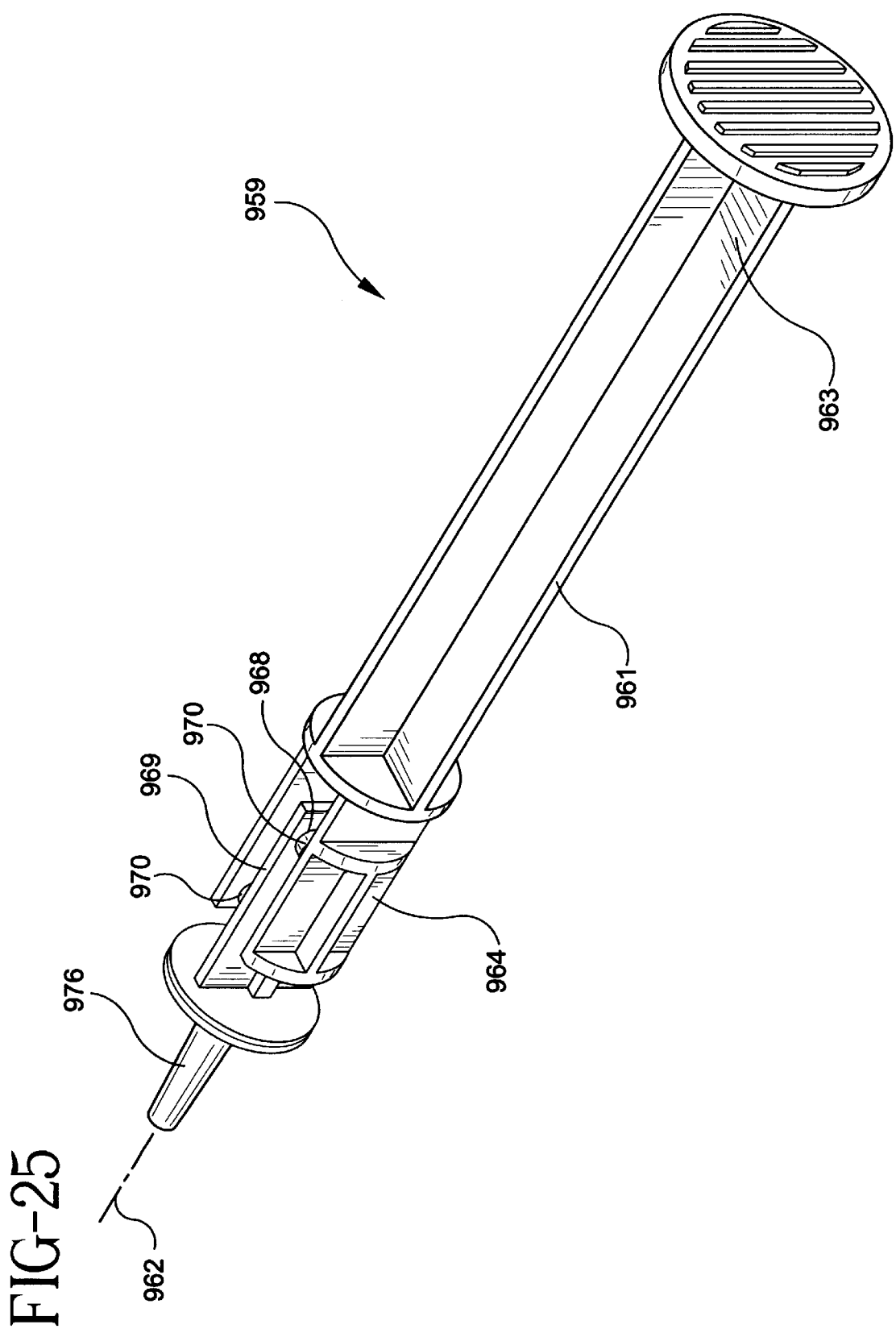
FIG. 25 is a perspective view of an alternative embodiment of the plunger of the present invention.

FIG. 25 illustrates an alternative plunger 959 including an elongated plunger rod 961, having a longitudinal axis 962, a proximal portion 963 and a distal portion 964 connected by a breakable connection 968. Either the proximal portion or the distal portion includes an axial projection 969 having at least one traverse protuberance 970 projecting therefrom. In this embodiment, the axial projection is part of distal portion 964 and the protuberance is connected to the proximal portion. The breakable connection is on the protuberance and in this embodiment it is generally in the area where the transverse protuberance joins the proximal portion. Although the plunger in the embodiment of FIG. 25 functions similarly to the plunger in the embodiment of FIGS. 21–23, the axial projection in this embodiment is on the distal portion while the axial projection in the embodiment of FIGS. 21–23 is on the proximal portion. Accordingly, either the proximal portion or the distal portion may include the axial projection having at least one transverse protuberance. In this embodiment there are four transverse protuberances, two of which project from one side of the axial projection and the other two transverse protuberances project from the other side of the axial projection.

Figure 26:
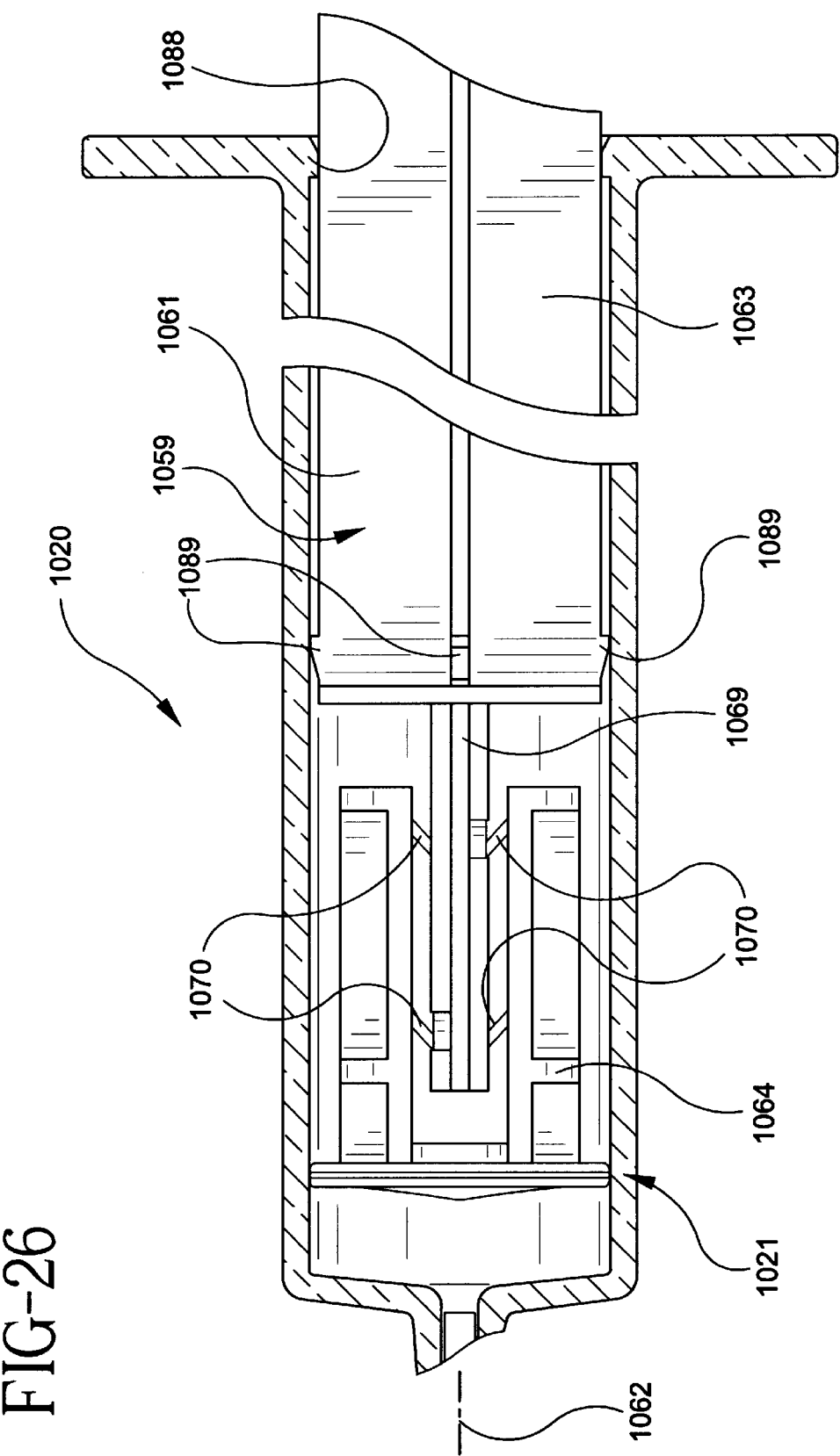
FIG. 26 is a partially cross-sectional side elevational view of an alternative embodiment of the present invention.

FIG. 26 illustrates another alternative embodiment of the present invention. In this embodiment the fluid delivery device is a syringe 1020 which functions similarly to the syringe of FIGS. 17–20. This syringe includes a barrel 1021 and a plunger 1059. The plunger includes a plunger rod 1061 having a longitudinal axis 1062, a proximal portion 1063 and a distal portion 1064 connected by a breakable connection. The proximal portion includes an axial projection 1069 having at least one transverse protuberance projecting therefrom. In this embodiment there are four transverse protuberances 1070 connected to the axial projection. The breakable connection is strong enough to hold the proximal portion and the distal portion together during normal use of the syringe and breakable upon application of an additional force applied to the proximal portion along the longitudinal axis. The breakable connection is on the protuberance. In this embodiment transverse protuberances 1070 project from the axial projection and they are inclined at an angle of approximately 45 degrees from longitudinal axis 1062. This configuration makes the breakable connection stronger and more able to resist an axial force applied to the proximal portion in a proximal direction than when an additional force is applied in a distal direction along the longitudinal axis. It is preferred that the additional force necessary to break the breakable connection be lower when applied in a distal direction than when applied in a proximal direction.

Syringe 1020 further includes means for holding proximal portion 1063 of the plunger rod in barrel 1021 after the breakable connection has been broken. This is an important feature of the present invention because after the breakable connection is broken it is possible for the proximal portion of the plunger rod to fall out of the barrel. It is preferred that the proximal portion of the plunger stay within the barrel so that the used syringe can be disposed of in its entirety. In this embodiment means for holding the proximal portion in the barrel includes an inwardly directed projection in the barrel and an outwardly projection on the proximal portion of the plunger rod. The inwardly directed projection on the barrel in this embodiment is annular ring 1088 at the proximal end of the barrel and the outward directed projection on the plunger rod comprises projections 1089. The projection on the plunger rod can be a continuous annular ring or one or more individual projections. Likewise, the inwardly directed projection in the syringe barrel can be an annular ring or one or more radially inwardly directed projections. The inside diameter described by annular ring 1088 is smaller than the outside diameter described by radial projections 1089 so an additional force is required to push the plunger past annular ring 1088 during assembly of the syringe. In this embodiment outwardly directed projection 1089 is saw-toothed or cam-shaped so that the force required to insert the plunger rod into the barrel through the interference provided by annular ring 1088 is less in the proximal direction than in the distal direction.

Figure 27:
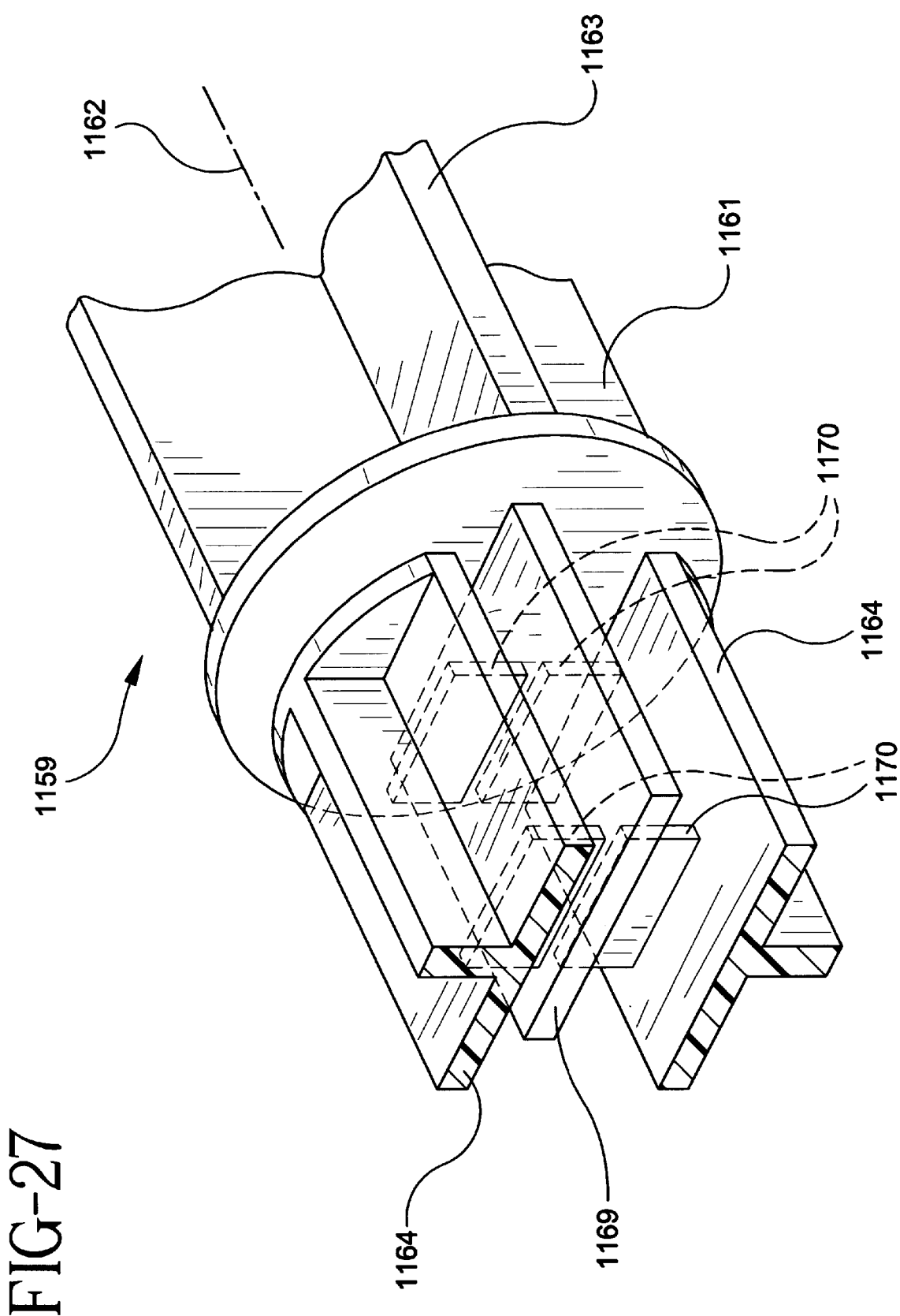
FIG. 27 is an enlarged partially cross-sectional view of an alternative plunger of the present invention.

FIG. 27 is another alternative embodiment of the plunger of the present invention. In this embodiment plunger 1159 includes elongated plunger rod 1161 having a proximal portion 1163 and a distal portion 1164. The plunger of this embodiment functions similarly to the plunger of the embodiment of FIGS. 17–20. Proximal portion 1163 of the plunger rod includes axial projection 1169 at its distal end having at least one transverse protuberance projecting therefrom. In this embodiment the axial projection is planar-shaped and has four transverse protuberances 1170 projecting from it and connected to the distal portion. In this embodiment, the transverse protuberances are planar-shaped and aligned substantially perpendicular to longitudinal axis 1162 of the plunger rod. A breakable connection is contained on the transverse protuberances. The breakable connection is strong enough to hold the proximal portion and distal portion together during normal use of the syringe and breakable upon the application of an additional force applied to the proximal portion along the longitudinal axis. This configuration of the proximal protuberances is desirable because the protuberances are easier to manufacture when the proximal portion, the distal portion and the protuberances are injection molded in a one-piece structure.

What is claimed is:
1. A syringe comprising:
   a barrel having a fluid chamber, a proximal end, a distal end and an elongated tip extending from said distal end having a passageway therethrough in fluid communication with said chamber; and a plunger including an elongated plunger rod having a longitudinal axis, a proximal portion and a distal portion connected by a breakable connection, one of said proximal portion and said distal portion including an axial projection having a plurality of transverse protuberances projecting therefrom, said protuberances being connected to the other of said proximal portion and said distal portion, said breakable connection being on said protuberances, said distal portion including a stopper slidably positioned in fluid-tight engagement with an inside surface of said chamber for drawing fluid into and out of said chamber by movement of said plunger relative to said barrel, said breakable connection being strong enough to hold said proximal portion and said distal portion together during normal use of said syringe and breakable upon application of an additional force applied to said proximal portion along said longitudinal axis.

2. The syringe of claim 1 wherein said transverse protuberances project from opposite sides of said axial projection.

3. The syringe of claim 2 wherein said axial projection includes four transverse protuberances.

4. The syringe of claim 3 wherein two of said transverse protuberances project in substantially the opposite direction from the other two of said transverse protuberances.

5. The syringe of claim 1 wherein said axial projection is planar shaped having two opposed side walls and at least one transverse protuberance projecting from each of said two side walls.

6. The syringe of claim 1 further including a distally directed extension shaped to fit within said passageway for displacing fluid from said passageway said plunger is positioned distally with respect to said barrel.

7. The syringe of claim 1 wherein said proximal portion, said distal portion and said breakable connection are integrally molded of plastic material.

8. The syringe of claim 7 wherein the plastic material has a modulus of elasticity within the range of about 800 MPa to 4000 MPa.

9. The syringe of claim 1 wherein said breakable connection is made of material selected from the group of polyethylene, polystyrene, polypropylene and adhesives.

10. The syringe of claim 1 wherein said stopper and said distal portion are integrally molded of plastic material.

11. The syringe of claim 1 wherein said additional force is a distally directed within the range of about 2.2 kg to 6.8 kg (5 pounds to 15 pounds).

12. The syringe of claim 1 further including a needle assembly including a cannula having a proximal end, a distal end and a lumen therethrough, a hub having an open proximal end with a cavity therein, and a distal end joined to said proximal end of said cannula so that said lumen is in fluid communication with said cavity, said needle assembly being connected to said barrel so that said elongated tip of said barrel is in said cavity of said hub.

13. The syringe of claim 12 wherein said cannula and said hub are integrally molded of plastic material.

14. The syringe of claim 12 further including a needle shield having an open proximal end, a distal end and a side wall defining a cavity, said shield being removably connected to said hub so that said distal end of cannula is contained within said cavity.

15. The syringe of claim 1 further including a cannula having a proximal end, a distal end and a lumen therethrough, said proximal end of said cannula being joined to elongated tip so that said lumen is in fluid communication with said passageway.

16. The syringe of claim 1 further including means for holding said proximal portion of said plunger in said barrel after said breakable connection is broken including an inwardly directed projection in said barrel and an outwardly directed projection on said proximal portion.

17. A syringe comprising:
a barrel having a fluid chamber, a proximal end, a distal end and an elongated tip extending from said distal end having a passageway therethrough in fluid communication with said chamber; and
a plunger including an elongated plunger rod having a longitudinal axis, a proximal portion and a distal portion connected by a breakable connection, one of said proximal portion and said distal portion including an axial projection having four transverse protuberances projecting therefrom, said protuberances being connected to the other of said proximal portion and said distal portion, said breakable connection being on said protuberances, two of said transverse protuberances projecting in substantially the opposite direction from the other two of said transverse protuberances, said proximal portion, said distal portion and said breakable connection being integrally molded of plastic material, said distal portion including a stopper slidably positioned in fluid-tight engagement with an inside surface of said chamber for drawing fluid into and out of said chamber by movement of said plunger relative to said barrel, said breakable connection being strong enough to hold said proximal portion and said distal portion together during normal use of said syringe and breakable upon application of an additional distally directed force applied to a proximal end of said proximal portion along said longitudinal axis.

18. The syringe of claim 17 further including a distally directed extension shaped to fit within said passageway for displacing fluid from said passageway said plunger is positioned distally with respect to said barrel.

19. The syringe of claim 17 further including a needle assembly including a cannula having a proximal end, a distal end and a lumen therethrough, a hub having an open proximal end with a cavity therein and a distal end joined to said proximal end of said cannula so that said lumen is in fluid communication with said cavity, said needle assembly being connected to said barrel so that said elongated tip of said barrel is in said cavity of said hub.

20. The syringe of claim 19 further including a needle shield having an open proximal end, a distal end and a side wall defining a cavity, said shield being removably connected to said hub so that said distal end of cannula is contained within said cavity.

21. The syringe of claim 17 wherein said additional distally directed force is within the range of about 2.2 kg to 6.8 kg (5 pounds to 15 pounds).

22. A plunger for use in a syringe barrel having a fluid chamber, a proximal end, a distal end and an elongated tip extending from the distal end having a passageway therethrough in fluid communication with the chamber comprising:
an elongated plunger rod having a longitudinal axis, a proximal portion and a distal portion connected by a breakable connection, one of said proximal portion and said distal portion including an axial projection having four transverse protuberances projecting therefrom, said protuberances being connected to the other of said proximal portion and said distal portion, said breakable connection being on said protuberances, two of said transverse protuberances projecting in substantially the opposite direction from the other two of said transverse protuberances, said proximal portion, said distal portion and said breakable connection being integrally molded of plastic material, said distal portion including a stopper for slidable positioning in fluid-tight engagement with an inside surface of a syringe barrel chamber for drawing fluid into and out of said chamber by movement of said plunger relative to said barrel, said breakable connection being strong enough to hold said proximal portion and said distal portion together during normal use of said syringe and breakable upon application of an additional force applied to a proximal end of said proximal portion along said longitudinal axis.

23. The plunger of claim 22 further including a distally directed extension shaped to fit within the passageway of an elongated tip of a syringe barrel for displacing fluid from said passageway when said plunger is positioned distally with respect to said barrel.

* * * * *